(12) United States Patent  (10) Patent No.: US 8,274,279 B2
Gies  (45) Date of Patent: Sep. 25, 2012

(54) INSPECTION APPARATUS AND METHOD

(75) Inventor: Paul D. Gies, Redwood Meadows (CA)

(73) Assignee: Athena Industrial Technologies, Inc. (CA)

( * ) Notice: Subject to any disclaimer, the term of this patent is extended or adjusted under 35 U.S.C. 154(b) by 270 days.

(21) Appl. No.: 12/445,802

(22) PCT Filed: Oct. 16, 2007

(86) PCT No.: PCT/CA2007/001836
§ 371 (c)(1),
(2), (4) Date: Apr. 16, 2009

(87) PCT Pub. No.: WO2008/046209
PCT Pub. Date: Apr. 24, 2008

(65) Prior Publication Data
US 2010/0207620 A1    Aug. 19, 2010

Related U.S. Application Data

(60) Provisional application No. 60/829,795, filed on Oct. 17, 2006.

(51) Int. Cl.
*G01N 27/82* (2006.01)
(52) U.S. Cl. .................. 324/240; 324/200; 324/243
(58) Field of Classification Search ............. 324/240
See application file for complete search history.

(56) References Cited

U.S. PATENT DOCUMENTS

| 1,944,954 | A | * | 1/1934 | Sperry | 324/226 |
|---|---|---|---|---|---|
| 2,065,119 | A | * | 12/1936 | Davis, Jr. | 324/241 |
| 2,067,804 | A | * | 1/1937 | Thorne | 324/217 |
| 2,103,224 | A | * | 12/1937 | Schweitzer et al. | 324/240 |
| 6,275,030 | B1 | | 8/2001 | De Haan | |
| 6,414,483 | B1 | | 7/2002 | Nath et al. | |
| 6,501,267 | B1 | * | 12/2002 | Kurokawa et al. | 324/242 |
| 6,534,970 | B1 | * | 3/2003 | Ely et al. | 324/207.17 |
| 6,954,064 | B2 | * | 10/2005 | Sergoyan et al. | 324/240 |
| 6,967,478 | B2 | * | 11/2005 | Wayman et al. | 324/238 |

(Continued)

FOREIGN PATENT DOCUMENTS

GB    2012431    8/1977

OTHER PUBLICATIONS

International Search Report dated Feb. 4, 2008, issued in corresponding international application No. PCT/CA2007/001836.

*Primary Examiner* — Jermele M Hollington
*Assistant Examiner* — Trung Nguyen
(74) *Attorney, Agent, or Firm* — Ostrolenk Faber LLP

(57) ABSTRACT

An apparatus and method are disclosed for detecting flaws in electrically conductive materials by observing properties of the back-EMF of the eddy current field generated by driving magnetic flux through the object to be examined. The input signal may include sweeps at several frequencies, and may do so at one time under the principle of wave superposition. The sectorial observations of eddy currents summations may be compared to a known datum for a defect free material, the presence of anomalies in eddy field back EMF divergence tending to provide an indication of an irregularity in the underlying eddy field, and hence in the underlying material itself. The portable unit may have a number of different configurations depending on the nature of the object to be examined, be it a flat or large radius plate, a flange, a rail, or some other structural element.

45 Claims, 14 Drawing Sheets

U.S. PATENT DOCUMENTS

| | | | |
|---|---|---|---|
| 7,579,831 B2* | 8/2009 | Zimmermann | 324/240 |
| 2002/0093330 A1* | 7/2002 | Crouzen et al. | 324/240 |
| 2002/0097045 A1* | 7/2002 | Crouzen et al. | 324/240 |
| 2002/0105324 A1* | 8/2002 | Kwun et al. | 324/240 |
| 2005/0237055 A1* | 10/2005 | Sun et al. | 324/240 |
| 2008/0018331 A1* | 1/2008 | Raulerson et al. | 324/240 |

* cited by examiner

INSPECTION APPARATUS AND METHOD

CROSS REFERENCE TO RELATED APPLICATIONS

The present application is a 35 U.S.C. §371 National Phase conversion of PCT/CA2007/001836, filed Oct. 16, 2007, which claims benefit of U.S. Provisional Application No. 60/829,795, filed Oct. 17, 2006. The PCT International Application was published in the English language.

FIELD OF THE INVENTION

This Application relates to inspection apparatus and methods for their use.

BACKGROUND OF THE INVENTION

Defect or anomaly detection in structures is often important in determining maintenance intervals, or for determining whether structures require repair or replacement. Non-destructive detection of structural anomalies may be desired, and the ability to perform timely and effective examination of objects may not necessarily be made easier when the objects are large, may be remotely located relative to large population centers, and may be subject to harsh geographic or climatic conditions.

By way of example, the inspection of pipelines is a task of some interest and economic importance to the owners and users of pipelines, and in particular as it pertains to pipelines for carrying hydrocarbon gases and oils, although pipelines for transporting other fluids and slurries are also known. A typical pipeline for carrying gas, oil or water may run for many miles between pumping stations. The pipeline may be exposed to the weather, and that weather may include a corrosive atmosphere, be it a salt spray environment or some other. The pipeline may run through regions of greater or lesser humidity, and the weather may vary from season to season between extremes of heat and cold. In some places the pipeline may be carried above ground on spaced supports. In others it may be buried, or partially buried. In locations in which the pipeline is buried, the surrounding stratum may have a high or low moisture content, and may be alkaline or acidic. The fluid, or slurry to be carried in the pipeline may itself not be benign, but may be of an aggressive nature, and may be abrasive or corrosive, or both. The material flowing in the pipeline may be under significant pressure, perhaps in the thousands of psi., and may be at an elevated temperature, possibly in the range of 80-100 C. This environment may effect not only the life of the pipeline and the nature of the defects that may be expected to be found in a section of pipe over time, but also the tools used for monitoring and maintaining the pipeline. Stress cracking and stress corrosion may occur or be hastened by movement related to temperature change, earthquakes or tremors, ground settling, vibration from fluid movement, and pressure changes in the medium during operation.

Even assuming that a region of interest has been identified, and, if necessary, that there has been digging to expose that region to permit access for inspection, the pipewall to be inspected may not be fully accessible. That is, the pipewall may be protected by an external covering or coating. Removal of the covering or coating may not be desirable or practical, and, once the inspection is complete, replacement of the removed covering or coating may not necessarily be an easy or inexpensive task. Further still, pipeline inspection may occur under less than optimal conditions. For example, inspection under wintry conditions may be particularly problematic. The inspector may be encumbered in bulky clothing. The use of writing instruments may be difficult. The inspector may be up to his or her waist in snow, on uneven terrain, with uncertain footing. The wind may be uncomfortably raw or brisk. At other times of year, the inspector may be beset by black flies. In short, pipeline inspection may be a miserable task, and the accuracy and reliability of the results may reflect this.

The foregoing discussion has been made in the context of pipelines. However, it might also be made in the context of other large structures—be they the hulls of ships, railroad car bodies, seagoing drilling or production platforms, rail road tracks (and railroad wheels, in situ), bridge structures, and so on.

SUMMARY OF THE INVENTION

In an aspect of the invention there is an anomaly detection apparatus that employs a magnetic flux emitting device to induce eddy currents in an electrically conductive object to be examined. The apparatus has a sectoral array of eddy current divergence sensors ranged about the magnetic flux emitting device, permitting sectoral variations in eddy current distribution to be observed.

In another aspect of the invention there an anomaly detection apparatus for placement next to an electrically conductive object. The apparatus includes an electromagnetic field emitting member, and a power source connected to the electromagnetic field emitting member. The power source is operable to drive the electromagnetic field emitting member to emit a time varying electromagnetic field. The power source has at least first and second driving frequencies. There is an array of electromagnetic field sensing members, the members of the array are mounted adjacent to the electromagnetic field emitting member. The array included at least first and second field sensing members. The first and second field sensing members are oriented toward non-coincident regions adjacent to the field emitting member. At least the first member is non-concentric with the field emitting member. Monitoring circuitry is connected to the members of the array. The monitoring circuitry is operable to observe differential variation of signals as between members of the array. A processor is operable to compare signals sensed at the members of the array in response to electromagnetic signals emitted at the first frequency and at the second frequency.

In another aspect of the invention there is a portable anomaly detection apparatus for inspecting an electrically conductive object. That apparatus has an electromagnetic field emitter operable to pass a time varying magnetic flux field through at least a portion of the electrically conductive object, thereby to generate an electrical eddy current field in the electrically conductive object. There is eddy current monitoring circuitry operable to survey at least first and second portions of the eddy current field, the first and second portions are non-coterminous. There is signal processing apparatus connected to the eddy current monitoring circuitry, the signal processing apparatus being operable to compare data received from the eddy current monitoring circuitry observed at the first and second portions of the eddy current field.

In a further aspect of the invention there is a mobile anomaly detector operable to survey an electrically conductive object. The detector has a shoe, the shoe having a sole for engagement with the object, and an electromagnetic field emitter mounted within the shoe. There is a power source connected to drive the emitter, the power source being operable at a plurality of frequencies. The emitter is operable to induce an eddy current field in the object when the sole is placed adjacent thereto. A plurality of eddy current sensors is arrayed adjacent to the electromagnetic field emitter. Members of the plurality of eddy current sensors are operable to monitor back EMF from different portions of the eddy current field. At least one of (a) a recorder operable to store recording data from the current sensors for subsequent signal processing operations; and (b) a processor operable to interpret data obtained from the eddy current sensors.

In a feature of that aspect of the invention, the sole has a profile constraining the detector to a single degree of freedom in translation, and the anomaly detector includes a plurality of the emitters. In another feature, the sole has a profile conforming to a rail road track rail. In still another feature, the plurality of emitters includes at least a first emitter and a second emitter, the emitters are movable relative to one another to permit the detector to girdle the object.

In still another aspect of the invention, there is a method of detecting anomalies in an electrically conductive object, the method comprises the steps of: establishing a time varying eddy current field in the electrically conductive object; monitoring at least first and second regions of the eddy current field, the first and second regions are non-coterminous and non-concentric; and comparing at least one of (a) eddy currents monitored in the first region with eddy currents monitored in the second region; and (b) eddy currents monitored in both the first region and the second region with a reference standard for the first region and the second region respectively.

In a feature of that method, the method includes monitoring total eddy current flux through a zone to be examined, and comparing that total eddy current flux to a sum of eddy current fluxes observed in discrete portions of the zone. In another feature, the method includes employing a magnetic flux emitting apparatus to establish the time varying eddy current field; monitoring total eddy current flux through a zone adjacent to the object to be examined, and comparing that total eddy current flux with a measured total emitted flux from the flux emitting apparatus.

In another aspect of the invention, there is a process of detection of anomalies in an electrically conductive plate. The process includes providing an anomaly detection apparatus having an electromagnetic field emitting member, a power source connected for powering the electromagnetic field emitting member, the power source are operable to cause the electromagnetic field emitting member to emit a time varying electromagnetic field. The power source has at least a first frequency and a second frequency. There is an array of electromagnetic field sensing members, the members of the array being mounted adjacent to the electromagnetic field emitting member. There is monitoring circuitry connected to the members of the array, the monitoring circuitry being operable to sense differential variation of signals as between members of the array. There is a processor operable to compare signals sensed at the members of the array in response to electromagnetic signals emitted at the first frequency and at the second frequency;

passing the anomaly detection apparatus adjacent to the electrically conductive plate. The process includes emitting electromagnetic field signals at more than one frequency from the electromagnetic field emitter to cause eddy currents to be generated in the electrically conductive plate; monitoring the eddy currents at a plurality of positions; and comparing data monitored at the plurality of positions and at the different frequencies to provide an indication of the location of an anomaly in the plate.

In a further aspect of the invention there is a hand portable eddy field anomaly detector. It has a magnetic field emitter operable to induce an eddy current field in an adjacent electrically conductive object to be examined; and sensing apparatus operable, while the detector is in one location, to sample at first and second sensing regions, back EMF of the eddy current field;

the first region are different from the second region. It includes at least one of (a) a recorder operable to store data observed with respect to the first and second regions; and (b) a signal processor operable to compare at least one of (i) data observed with respect to the first region and data observed with respect to the second region; and (ii) data observed with respect to at least one of the first and second regions and a reference datum. The first and second regions satisfying at least one condition selected from the set of conditions consisting of (a) the first region includes at least a portion not covered by the second region, and the first and second regions are non-concentric; (b) the first region includes at least a portion not covered by the second region, and the second region includes at least another portion not covered by the first region; and (c) the first and second footprints are non-concentric and at least one of the first and second regions is eccentric relative to the magnetic field emitter.

In a feature of that aspect of the invention, the sensing apparatus includes at least one of (a) an array of discrete sensors each having a different footprint; and (b) a movable sensor locatable in a plurality of different sampling positions while the detector remains in one place. In another feature, the sensing apparatus includes a sensor movable between at least a first position and a second position while the detector remains in one place. In a further feature, the emitter includes a magnetically permeable core having a centerline axis, and the movable sensor is angularly displaceable on an arc centered on the centerline axis. In still another feature the apparatus includes an array of discrete sensors each having a different footprint. In a further feature, the array of discrete sensors extends in a substantially annular pattern. In a still further feature, the array of discrete sensors includes a plurality of sensors defining segments of a substantially annular footprint. In still another further feature, the array of discrete sensors includes a plurality of sensors defining n segments about a central axis, the n segments are spaced on an angular pitch of 360/n degrees about the central axis. In yet another feature, the array of discrete sensors includes a plurality of sensors defining n segments about a central axis, the n segments each subtending an angular arc of n/360 degrees +/±20%.

In another feature of that aspect of the invention the detector includes a magnetically permeable core having a pole piece and a co-operating peripheral wall spaced from the pole piece. In still another feature the detector has a foot for placement against an object to be examined, and the foot is selected from the set of feet consisting of (a) a substantially planar base; (b) a chamfered base; and (c) a base having a contoured profile. In another feature, the foot is chamfered and includes a first portion and a second portion, each of the first and second portions of the foot including members of the sensing apparatus, and the first and second portions lying to either side of the chamfer. In another feature, the base has a profile defining a portion of a cylindrical surface. In a further feature, the base has a profile defining a portion of a circular cylindrical surface.

In yet another feature, the detector weighs up to 20 lbs. In a still further feature, the apparatus includes a sensing module for passing next to an object to be examined, and the sensing module weighs up to 5 lbs. In still another feature, there is a hand held sensing module for passing next to an object to be examined, and a display, the detector having a processor operable to present anomaly identification indicia on the display. In another feature, the display includes an anomaly depth indicator. In a further feature the display includes an anomaly position indicator. In a still further feature, the display includes an anomaly direction indicator. In yet another feature, there is a photographic recording medium. In still yet another feature there is an audio recording medium. In still yet another feature, there is telemetry apparatus. In still another feature the apparatus includes incremental change of position apparatus.

In another feature, the apparatus has a chassis having a carrying handle, a power supply mounted to the chassis, a display mounted to the chassis, and a removable hand sensor. In another feature, there is a controller operable to drive the emitter at more than one frequency. In a further feature, the controller is operable to drive the emitter at a plurality of frequencies simultaneously. In still another feature, the apparatus includes a sensor mounted to measure total emitted magnetic flux from the emitter. In another feature the apparatus includes a sensor located to monitor total eddy current back EMF. In a further feature, the apparatus includes a sensor mounted to measure total emitted magnetic flux from the emitter, a further sensor located to monitor total eddy current back-EMF; and a processor operable to compare total emitted magnetic flux to total eddy current back EMF.

BRIEF DESCRIPTION OF THE DRAWINGS

The invention may be explained with the aid of the accompanying illustrations, in which:

FIG. 3b shows another general arrangement view of the anomaly detection apparatus of FIG. 3a;

FIG. 5b shows a detail of one sector of the illustration of FIG. 5a;

FIG. 6 is a schematic signal processing elements of the apparatus of FIG. 3a;

FIG. 7a shows a diametral cross-section of an alternate embodiment of anomaly detection apparatus to that of FIG. 3a;

FIG. 8a shows a transverse cross-section on the centerline of a module of another alternate embodiment of anomaly detection apparatus to that of FIG. 3a;

FIG. 8b shows a side view on a longitudinal central cross-section of the embodiment of anomaly detection apparatus of FIG. 8a;

FIG. 10b shows a transverse cross-sectional view through the pipe and anomaly detection apparatus of FIG. 10a on section '10b-10b' of FIG. 10a.

FIG. 11a shows a cross-section, similar to FIG. 10b, of an alternate anomaly detection apparatus to that of FIG. 10a.

DETAILED DESCRIPTION

Figure 1:
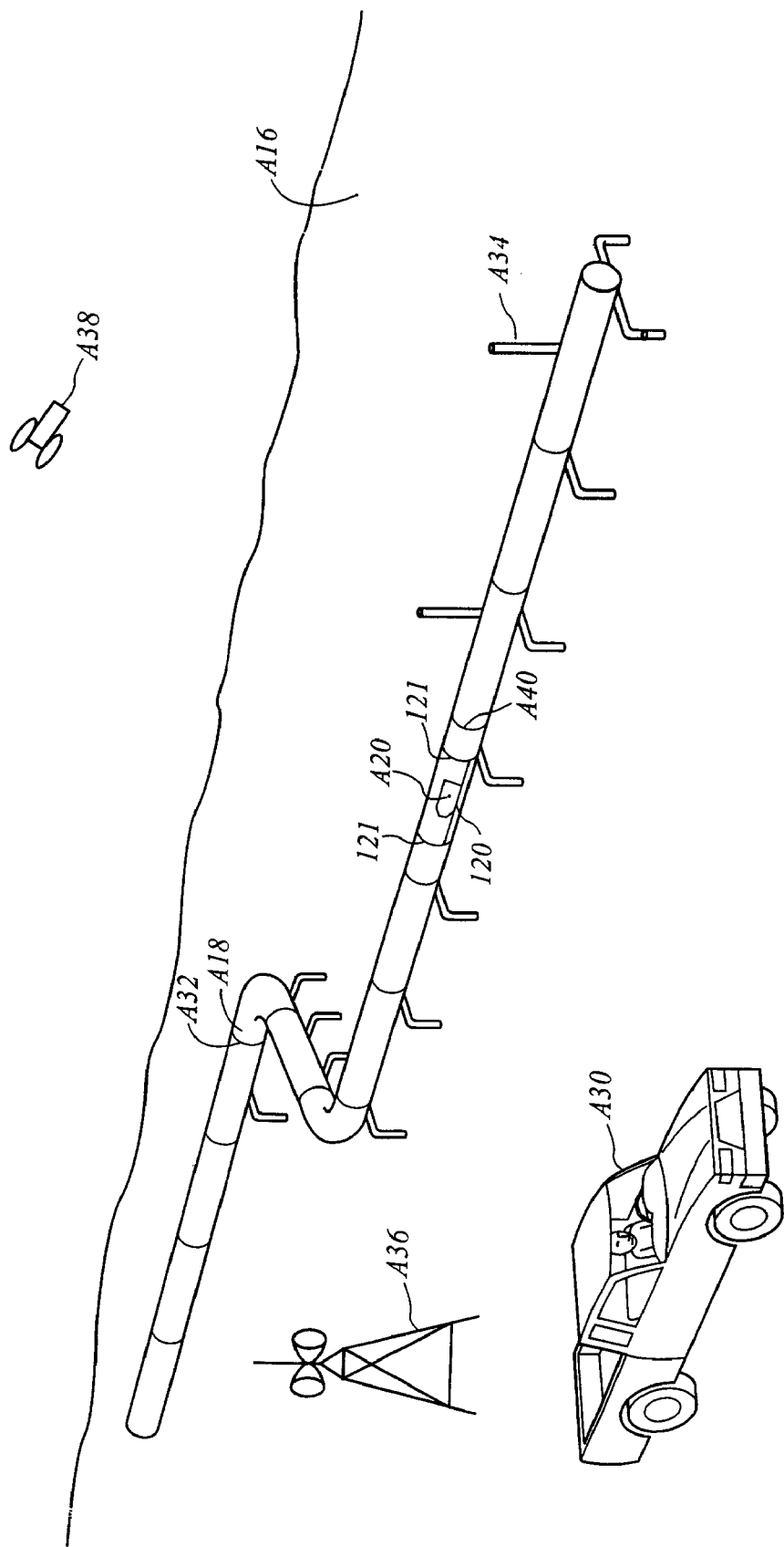
FIG. 1 shows a geographic region in which an anomaly detection tool as described herein may be employed.
Figure 2:
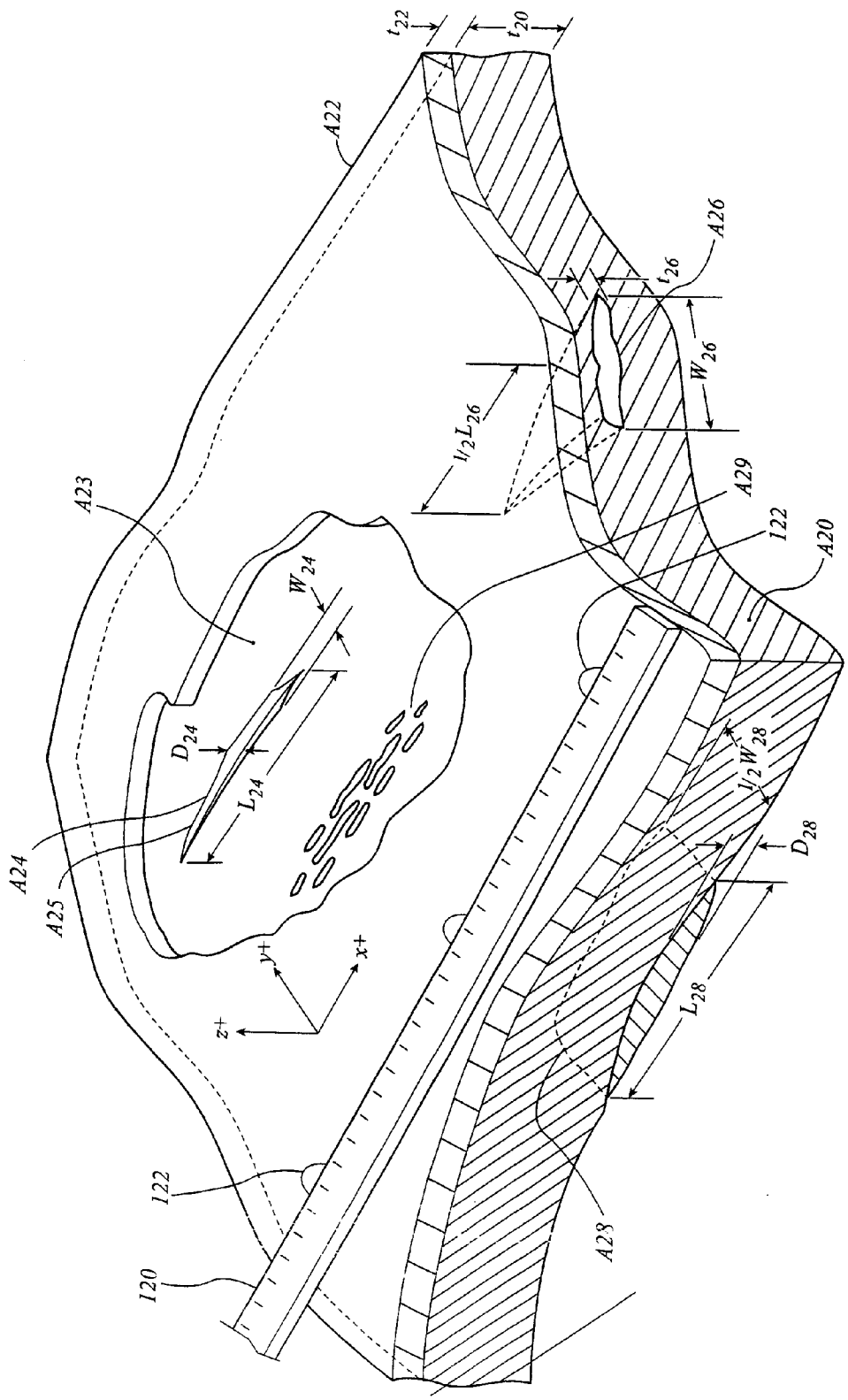
FIG. 2 shows a portion of a region of an object such as may be subject to inspection with an anomaly detection tool.
Figure 3A:
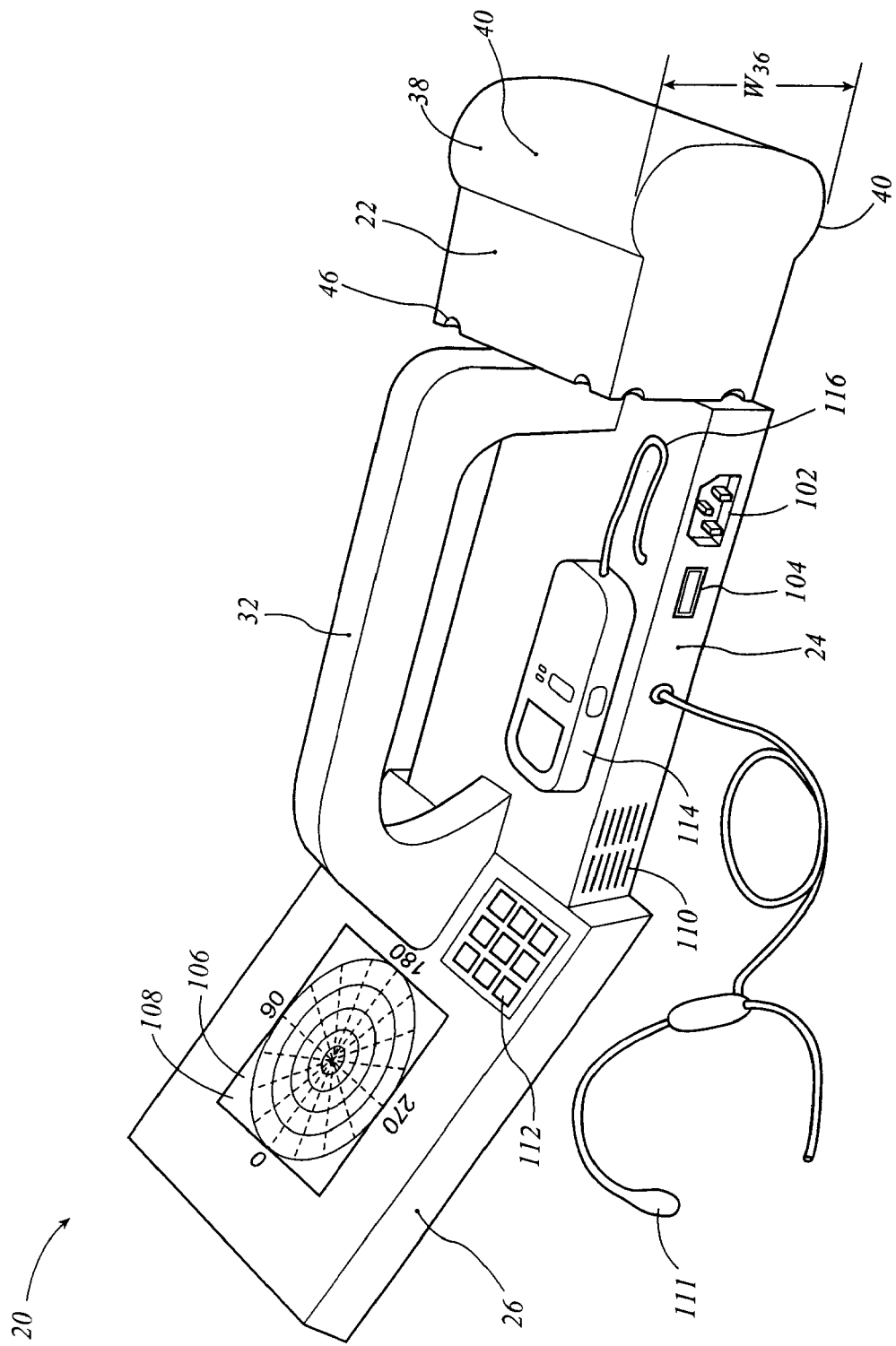
FIG. 3a shows a general view of an anomaly detection apparatus such as may be used to inspect the object of FIG. 2.
Figure 3B:
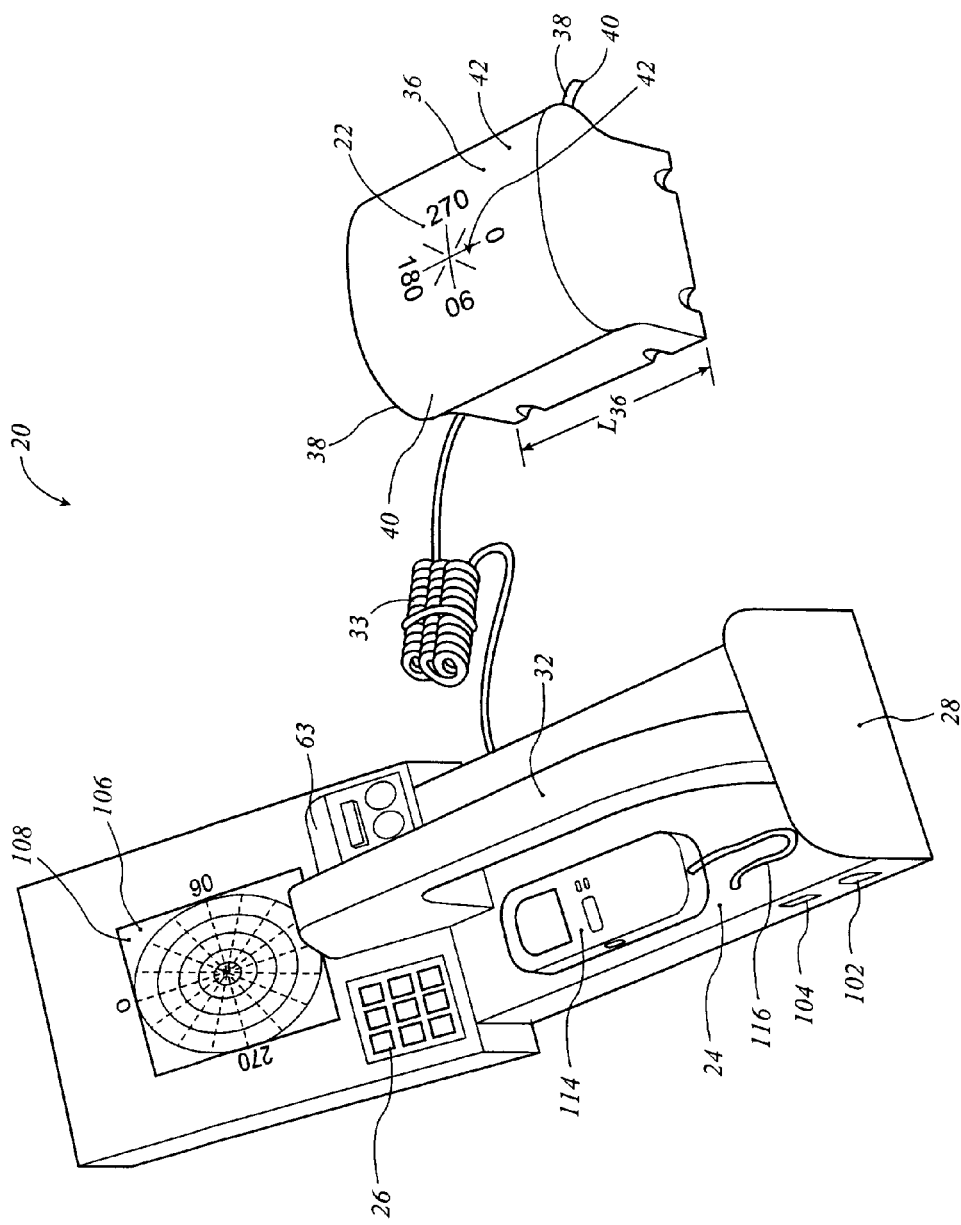
Figure 3C:
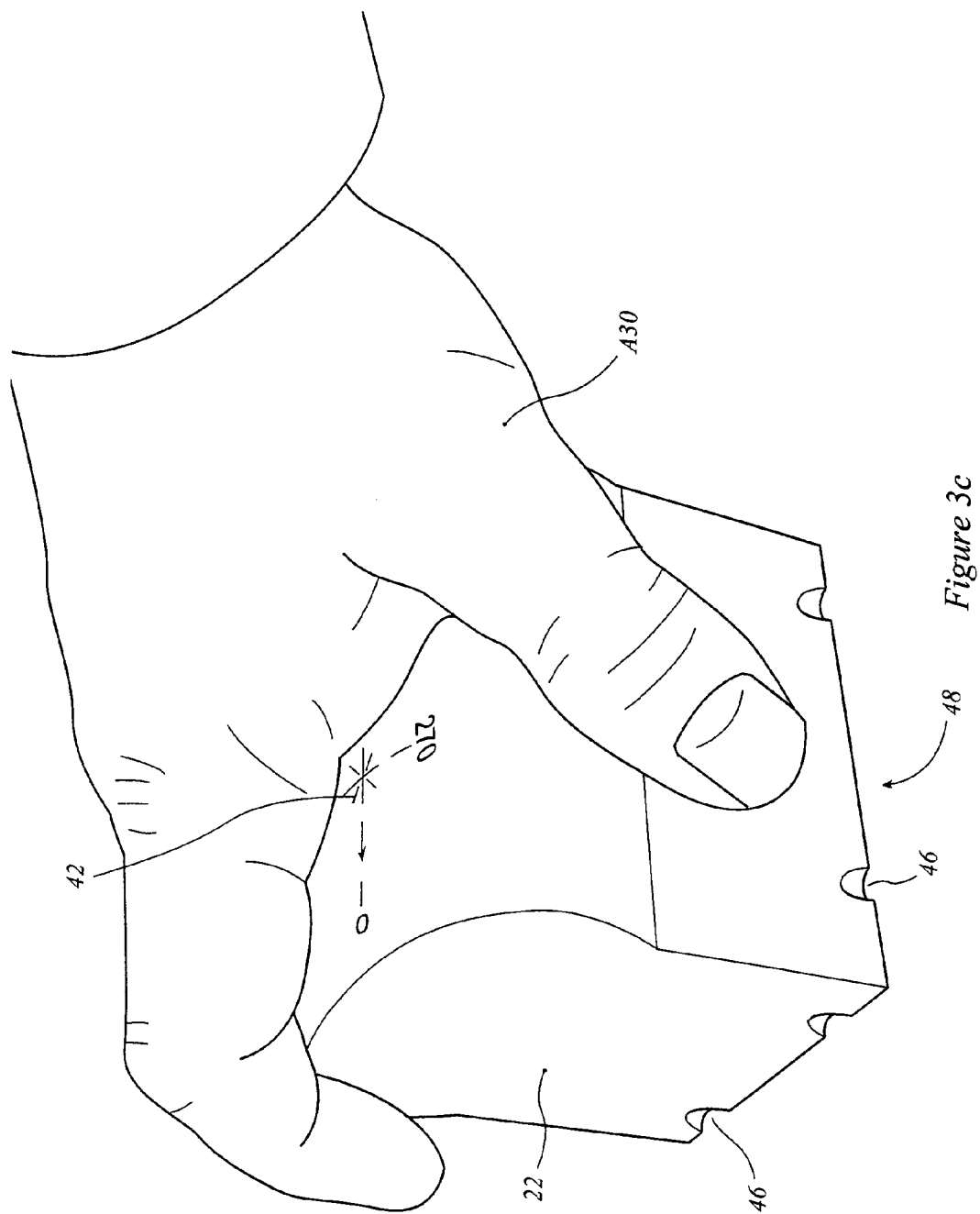
FIG. 3c shows a further view of a portion of the anomaly detection apparatus of FIG. 3a as hand held.

The description that follows, and the embodiments described therein, are provided by way of illustration of an example, or examples, of particular embodiments of the principles of the present invention. These examples are provided for the purposes of explanation, and not of limitation, of those principles and of the invention. In the description, like parts are marked throughout the specification and the drawings with the same respective reference numerals. The drawings are not necessarily to scale and in some instances proportions may have been exaggerated, the more clearly to depict certain features of the invention.

The terminology used in this specification is thought to be consistent with the customary and ordinary meanings of those terms as they would be understood by a person of ordinary skill in the art in North America. Following from the decision of the Court of Appeal for the Federal Circuit in *Phillips* v. *AWH Corp.*, the Applicant expressly excludes all interpretations that are inconsistent with this specification, and, in particular, expressly excludes any interpretation of the claims or the language used in this specification such as may be made in the USPTO, or in any other Patent Office, other than those interpretations for which express support can be demonstrated in this specification or in objective evidence of record in accordance with In re Lee, (for example, earlier publications by persons not employed by the USPTO or any other Patent Office), demonstrating how the terms are used and understood by persons of ordinary skill in the art, or by way of expert evidence of a person or persons of experience in the art.

By way of general overview, the apparatus described herein includes a sensing assembly for detecting anomalies in an electrically conductive material. The sensor may be, or may include a hand held inspection unit. The inspection unit may have an exciter coil that, in use, exposes the material to be inspected to a time varying magnetic field; a coil for measuring total eddy current flux in the object to be examined; and a sectoral coil or coils for measuring local differences, or divergences in eddy currents in portions of the induced field in the object to be inspected. The inspection unit includes electronic signal processing equipment such as may be operated to induce and to analyse data resulting from magnetic fields of multiple frequencies, such as may permit an assessment of the depth of anomalies in the object to be examined. The inspection unit may also include a data processing capability to permit eddy field anomaly data taken at several locations to be correlated in a manner tending to permit estimation of the location, size, shape, and nature of anomalies detected in the substrate. The apparatus may include a real time display that may permit an operator to observe where an anomaly may be located. Operation may be in either a freehand mode, in which the operator may, with the aid of a display or other feedback means, follow the physical extent of an anomaly. In a restrained or guided method of operation, the apparatus may be operated at a constant sweep speed along a known path, or may be moved in discrete increments along a known path, either linearly along a single path, or in a two dimensional sweep of continuous or discrete observation points. The operation may include a fast sweep or survey at a small number of frequencies (e.g., 3 frequencies). An area of interest, such as may be identified by a coarse or fast sweep, or other means, may be subject to a slower or more detailed sweep at a larger number of frequencies or finer spacing increments. A fine survey may follow a coarse survey.

To begin generically, a structural element A20 may typically be considered to be a portion of a plate or shell. It may be a portion of a length of pipeline, or a plate of a ship's hull, or a railroad track, or a pressure vessel body, a portion of a drill rig, a portion of a railroad car, a rail road car wheel tread, or another structural plate or wall. In general, in some embodiments the object may tend, conceptually, to be a web or membrane that has relatively great extent in two directions (x and y in a Cartesian co-ordinate context) such as might apply to a ship's plates, or longitudinal and circumferential, as might apply to a pipeline or pressure vessel, and of lesser extent in the third direction, namely that of plate thickness (the z direction in a Cartesian context, radial in a Polar co-ordinate context). Although structural element A20 may have the properties of a web or membrane for some purposes of structural analysis, (e.g., the wall of a pipeline or other pressure vessel) it will be assumed to have a finite, non-trivial thickness at the level of defect or anomaly detection that is of interest. It may be that examination is intended to reveal defects before a critical flaw size is reached.

Structural element A20 is electrically conductive, although it need not necessarily be ferro-magnetic and may be a semi-conductor or other partially conductive material, e.g., it may be made of a non-magnetic metal such as aluminum, or it may be a substrate of a semi-conductor material, or a partially or modestly conductive material such as a carbon fibre cloth or mat. Element A20 may have a protective coating A22. Protective coating A22 is assumed for the purposes of this description to be electromagnetically inactive: it is neither ferro-magnetic, nor a conductor of electricity. Protective coating A22 is also assumed to be of a substantially uniform thickness, $t_{22}$, and it is assumed that $t_{22}$ is small, if not very small, as compared to the wall thickness of the plate to be measured, $t_{20}$. For whatever reason, it may not be desirable to remove coating A22. However, somewhere in element A20 there may be an anomaly A25 such as a flaw or defect that may, potentially, hold the seeds of catastrophic failure. It would, therefore, be desirable to find such a flaw or defect. For example, suppose that element A20 has an anomaly in the nature of a crack A24 that initiated at a crack initiation site on the outside or external surface A23 of element A20, and that has now grown to a certain size signified by length, $L_{24}$, and depth, $D_{24}$. Suppose also that element A20 has another anomaly in the nature of a void or an inclusion A26 that, again, may be located a certain depth from the surface and may have a certain width $W_{26}$, breadth $t_{26}$ or and length, $L_{26}$. Further still, it may be that element A20 has an anomaly in the nature of a region of corrosion A28, in which a portion of the material adjacent to the inside or outside surface has been transformed to a non-conductive oxide, that region having an average depth, $D_{28}$, length, $L_{28}$, and width $W_{26}$. Region A28 may be on either the inside or the outside of the plate. Alternatively, the defect may be a zone of defects such as a colony of stress corrosion cracks, as at A29.

For the purpose of this description, it will be assumed that structural element A20 is a portion of a large engineering structure A18, located in a relatively remote area A16. That is, it may be a portion of a pipeline A32 to which an inspector A30 has been sent. It may be that there has been a preliminary survey, such as by an internal pipeline pig that suggests that closer inspection of the region of pipeline A32 in the region of element A20 may be merited, or it may be that element A20 lies in a region in which high stress corrosion cracking may be expected, such as at a sharp bend. To the extent that element A20 may have been a portion of buried pipe, there may have been local excavation to expose the region of element A20 such as to permit inspection.

The location of element A20 may be recorded by hand on a reference map by inspector A30. However, it may be that the location of element A20 may be established to a relatively high level of accuracy by obtaining either optical or electronic survey fixes on points of known location, whether survey marks, mileposts A34, radio or microwave transmission towers A36, or satellite fixes A38, of which the most ubiquitous example is the US global positioning system, or GPS. Another method for correlating position is to use the nearest pipe joints A40 as a standard reference location, the location of the pipe joints relative to a known position being relatively easily and unambiguously determinable, while also being suitable for correlation to internal pipeline data logging as by a pipeline inspection pig data record.

The inspector A30 may employ a portable anomaly detection apparatus, such as may also be termed defect detection tool 20 for the purpose of investigating element A20 for anomalies A25. Tool 20 may be a portable tool, and may be a hand held tool, such as may weigh less than 10 lbs, and preferably less than 2 lbs., and which may be smaller in extent than one foot square, and preferably smaller in plan view than about 20 inches×6 inches. A portable unit may tend to be a unit that, in total, weighs less than about 20 lbs, and that can be carried into position, and be operated by, one person of average size and strength. Tool 20 may include hand held sensor assembly 22, a chassis 24 that may contain portable power source, a display unit 26, and a reference gauge element, or gauge plate member 28. The unit may include a handle, 32, by which it may be carried. Sensor assembly 22 may be connected by a cable 33 to a power supply 34. Power supply 34 may be carried in a vehicle or in a back pack or other man-portable configuration, or may be mounted to or within chassis 24. In one embodiment, the power supply may be included in the hand held sensor assembly.

Hand held sensor assembly 22 may have a housing 36 into which the various internal components, described below, are mounted. Housing 36, or the backshell portion thereof, 42 may be of a size and shape to fit in an operator's hand, and may have a grip 38, which may have the form of a moulded contour or contours 40 on opposed external regions thereof. The overall width $W_{36}$ of housing 36 in the opposed handgrip direction may be less than 6 inches, and may be less than 4 inches. Housing 36 may have a similar length. Sensor assembly 22 may weigh less than 5 lbs. In one embodiment assembly 22 may have a shape generally resembling a bread-loaf or a mushroom with a broader hand grip portion surmounting a generally narrow main body portion. Assembly 22 may include one or more orientation indicia 42, such as an arrow, a top center mark, a North, or 12 O'clock indication or a similar feature, by which the operator may understand the orientation of the device when viewing displayed real time output. Housing 36 may also have one or more indexing fittings 46 such as may be employed in making incremental traverses of the work piece. Index fitting, or fittings, 46 may include, for example, a male of female detent member, a rack, or a set of splines, and may be located in a first position for making one type of traverse, e.g., longitudinal relative to the major dimension of the object to be examined, and in a second position for making a traverse in another direction, be it a perpendicular direction such as transverse or circumferential. A very simple type of detent involves a ball bearing, which may be spring loaded, mounted amidst a straight edge. A mating member may have v-notches and a mating straight edge, and the loaded ball may seat in the V-notches when engaged.

Opposite backshell portion 42, sensor assembly 22 may have a sensing end, or sensing region or base, identified as 48. Housing 36 may have an accommodation 50 in which to seat a magnetic core element (or assembly of elements, as may be) designated as core 52. Core 52 may be made of highly magnetically permeable materials such as might be suitable for use in electrical transformers, whether a high resistivity ferrite material, or an iron, iron powder, or iron-nickel based alloy. Magnetic core 52 may include a central pole piece 54, a back plate portion 56, and a peripheral wall member 58. These members 54, 56 and 58 are made of highly magnetically permeable material, or materials, and form a continuous high permeability path. Central pole piece 54 may be hollow, or solid and may be substantially cylindrical. Plate portion 56 may have the form of a substantially circular disc. Peripheral wall 58 may have the form of a cylindrical ring. Pole piece 54 and peripheral wall 58 may stand away from plate 56 and have extremities 55 and 59 distant therefrom. Core 52 may be referred to as a magnetic flux focussing core. Peripheral wall 58 may be termed a flux focussing wall. That, is, since wall 58, pole piece 54, and back plate portion 56 form a continuous, high magnetic permeability path (as compared to the relatively low permeability path of the surrounding air), the free magnetic flux field that may form the remainder of the magnetic circuit may tend to be most concentrated in terms of flux density in the gap 'G' between the two "poles" defined by the central core and the outer peripheral wall. Thus, in a sense, the peripheral wall causes the magnetic flux to be "focussed" in the gap. The peripheral wall need not be fully continuous, or fully peripheral to obtain at least some of this beneficial focusing effect. It is, however, convenient that the wall be continuous, and form a closed periphery. It may also convenient that the pole piece and wall be of a relatively easily analyzed geometry in terms of facilitating post processing computation. Circular shapes with a regular, annular gap with a relatively uniform radial flux field may often tend to be more readily amenable to classical analytical calculations than entirely arbitrary geometric shapes. That is, it is mathematically convenient, though not necessarily mathematically necessary, that annular wall member 58 be concentric with central pole piece 54, and that the gap be a circular annulus that is also concentric therewith.

At least a portion of core 52 carries an element 60 operable to induce a magnetic field therein, the combination then being co-operable to define a magnetic flux field emitter. A relatively convenient example in this regard may be a central or main core winding wound about a portion of central pole piece 54 and identified as exciter coil 62. Exciter coil 62, and all other electrically powered elements of sensor assembly 22 may draw power from power supply 34. Although core 52 may be any arbitrary shape, and might be square or rectangular, it may be that core 52 may be taken as being a body of revolution whose elements are substantially circular in shape, and have a center line or axis of symmetry identified as CL. As a matter of rough estimation, where it is desired to examine the through thickness of a plate, for example, the outer diameter of peripheral wall member 58 may tend to be at twice as great, or greater, than the thickness $t_{20}$ of the plate, e.g. item A20.

Power supply 34 is operable to produce a time varying voltage and current through exciter coil 62. For the purpose of this description it may be taken that these time varying signals are electrical currents that vary sinusoidally, and that have a frequency. It may be possible to provide software capable of generating, and analysing feedback arising from, non-sinusoidal time varying wave forms, and even asynchronous, non-periodic, randomly generated time varying signals or pulses. However, for simplicity of operation and ease of description, it may be that the wave forms generated are periodic, with a constant frequency for a particular wave train, and a constant amplitude and wave shape (whether a spike, a square wave, a sawtooth, or, more typically, a sinusoid) and wavelength from peak to peak. Power supply 34 is capable of producing time varying power signals in a wide range of frequency bands. Power supply 34 may include a portable DC source, such as rechargeable batteries. While it may be typical that the signal processing or solid state conversion, or inversion, undertaken to produce these wave trains may occur in the main chassis item 24, this conversion or inversion could also occur in the remote hand set. Tool 24 may include a keypad or other input device 61 by which to turn the unit on, and to select the mode in which it operates. The input device 61 may permit the selection of frequency ranges, or such ranges may be self-selected by apparatus 20 based on feedback observation and control software. Tool 24 may also include a visual display or screen 63 by which the status of inputs may be seen or verified.

The time varying electrical signal passed through exciter coil 62 may tend to generate a corresponding time varying electromagnetic field in, and about core 52. Assembly 22 may include a sensor operable to measure the magnetic field induced in core 52 by the power signal received from the power supply. An example of such a sensor is a second winding, which may be termed a drive reference coil 66. Drive reference coil 66 may be mounted adjacent to, and coaxially with, exciter coil 62. In some embodiments, the windings of drive reference coil 66 may be intertwined with or wound about the windings of exciter coil 62. The signal monitored at the ends of drive reference coil 66 may be expected to correlate very closely to the magnitude and time variation of the magnetic field produced by the emitter, (i.e., by exciter coil 62 driving core 52) and may thus provide both a measure of the emitted magnetic flux field driven by coil 62, and may also serve as a feedback sensor providing information to the controller upon which the power signal to coil 62 may be controlled.

Sensor 22 may include a radial flux sensor. In one embodiment, this radial flux sensor may be termed a total energy reference coil 68. Coil 68 may have the form of an annular winding mounted concentrically about axis CL, adjacent to, or very nearly axially flush with the ends of pole piece 54 and annular peripheral wall 58, such that when sensor 22 (and hence the end of core 52) are placed in close proximity to element A20, flux moving radially in gap 'G', or closely adjacent thereto, may tend to cause a current to be generated in coil 68 (which is generally circumferential, and hence perpendicular to that flux). Although coil 68 may be placed anywhere in gap 'G' intermediate the inner and outer members of core 52, it may be convenient that it be placed at the mid-way radius. The flux sensed across the terminals of coil 68 may tend to be a measure of the total flux passing in gap 'G', both due to the imposed emitted flux field driven by exciter coil 62 in core 52, and also due to the opposing back-EMF of such eddy currents as may be induced in the underlying object to be examined.

Figure 4:
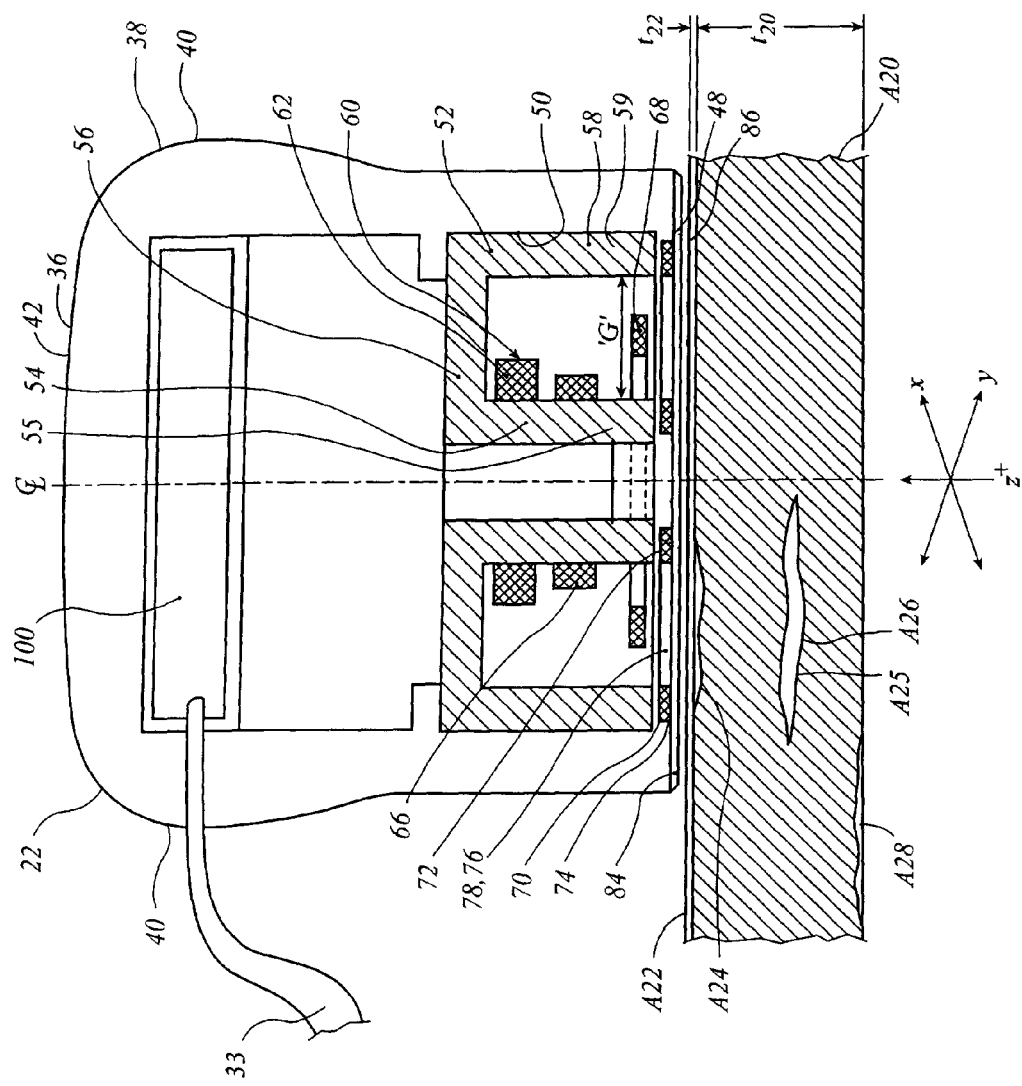
FIG. 4 shows a cross-sectional representation of the handheld portion of the anomaly detection device of FIG. 3a as positioned next to the object of FIG. 2.

Hand held sensor 22 may also include a set, group, or array of sensing loops 70. Loops 70 may be termed eddy field divergence sensor coils. Loops 70 may be arranged in a pattern about center line axis CL. Each of loops 70 may have its own unique footprint when viewed in plan form whether square, or round or triangular, or some other shape, and the loops may overlap, may have different shapes, and so on. However, while this may be true in the general sense, for ease of construction and subsequent analysis of observed results, it may be convenient for loops 70 to be arranged about center line axis CL in a regular or symmetrical pattern that is centered on axis CL, and for each of the loops to encompass a sector of an annulus in that pattern. The sectors may meet, or slightly overlap. Each loop may have four portions or legs, such as may be identified as a first, radially proximate or inner circumferentially extending arcuate leg 72, a second, or outer radially distal circumferentially extending arcuate leg 74, a first radially extending leg 76, and a second radially extending leg 78 circumferentially spaced from leg 76. Legs 72, 74, 76 and 78 co-operate to form a continuous winding having terminals 80 and 82 across which an output voltage $V_{70}$ may be sensed. Although each loop 70 may have as little as a single turn, it may be expected that each loop may be a multi-turn loop of fine wire. Alternatively, loop 70 may have the form of loops printed on a multilayer printed circuit board. Leg 72 may underlie core 52 in the axial direction, and leg 74 may underlie peripheral wall 58 in the axial direction. It may also be that each loop 70 may tend to lie in a plane substantially perpendicular to the center line axis CL, and flush, or very close to flush with the ends of core 52 and outer peripheral wall 58. For the purposes of clarity of illustration and ease of explanation, the axial spacing of features in FIG. 4 is exaggerated, somewhat in the manner of an exploded view. As assembled, loops 70, coil 68, and ends 55 and 59 may be substantially co-planar. The sensor coils, i.e., items 66, 68 and 70, are made of non-ferro magnetic material.

The internal components of the handset may be contained within the backshell by a cover member or closure member or faceplate 84. Faceplate 84 may also be referred to as a shoe, or sole-plate. Faceplate 84 may be quite thin, since it is generally desirable that the air gap in the axial direction be relatively small between core 52 and the object to be examined, structural member A20. Faceplate 84 may be formed from a non-participating medium, be it an electrically and magnetically transparent plastic, (such as Nylon™), metal, (such as zirconium), or some other material. Faceplate 84 may have a front face, or external surface 86 that defines the contact interface of hand held sensor 22, that rides upon the surface of the object to be examined. Faceplate 84 may be made of, or have a surface coating of, an abrasion or wear resistant material such as zirconium, zirconium nitride or zirconium oxide. It may be that faceplate 84 is made of a consumable material, and may be replaced from time to time as necessary. Alternatively faceplate 84 may carry a consumable surface film, coating or sheet, that covers faceplate 84 generally, and that may be replaced as required. In one embodiment, faceplate 84 may be made of a Nylon™ sheet. In another embodiment, faceplate 84 may be a zirconium sheet, or a quartz sheet, or other suitable material.

Apparatus 20 may also include a drive signal controller 92, an amplifier 90, and monitoring circuitry 94. Drive signal controller 92 may produce and control the strength and polarity of the desired waveform for exciting the test object, and amplifier 90 may amplify that signal to an appropriate power level for driving exciter coil 62 given the sample thickness, the frequency, and the size of the coil and core. Both signal controller 92 and amplifier 90 draw their power from power supply 34. Monitoring circuitry 94 includes contacts connected between the ports (i.e., voltage taps) on the various loops 70, and on coils 66 and 68, and ports of a signal processor 96. A signal recording device, or electronic data storage medium 98 may be provided, either to record analogue signals observed at loops 70 directly, or to record digitized data converted from those analogue signals, or to record partially or fully processed data, or all three. It may be that processor 96 is a digital signal processor that receives analogue output from the eddy current divergence sensors (i.e., loops 70), or it may be that an analogue to digital converter 93 is placed between the sensors and the processor, whether at the sensor end or at the processor end. Circuitry 94 is also connected to monitor the drive reference coil and the total energy reference coil. Circuitry 94 may include signal amplifiers 95 such as may be used to boost the raw signals at the various sensors.

Some or all of this signal processing apparatus may be located in the handheld sensor portion itself, or it may be that the processing equipment is carried in the portable processor chassis, item 24. It may be that the heavier items—such as the main power supply 34, the electronic data storage medium 98, and the main processor 96, are mounted in the processor chassis 24, while initial amplification of the analogue signals observed by loops 70 and the analogue to digital conversion occurs in a sub processor 100 contained within backshell 42 of handset 22.

Power supply 34 may be carried in the portable processor chassis 24, and may include a set of rechargeable batteries, preferably ones having a service life of four hours or more. Alternatively, power supply 34 may include an external power source connection, or charging connection 102 at which an external power source may be connected. Power supply operation may be governed by a power supply controller that is operable at the instance of the operator to work in one or another of the service modes indicated below, and that may include a variable frequency solid state power inverter capable of producing synthetic AC for driving the exciter coil 62. The power signal may be carried to hand held sensor 22, and return signals may be carried from hand held sensor 22 by wire or cable, 33. Chassis 24 may also have a data download port 104, by which data may be extracted for transfer to other data processing equipment or storage media. Port 104 may be a USB port.

Immediate, or substantially immediate real-time output may be provided by a display screen module 106 mounted to main chassis 24, and connected to signal processor 96. Screen module 106 may include a visual display 108. Visual display 108 may include a representation of the segmented sectoral footprint of the array of eddy current divergence sensors, namely loops 70, with the North or 12 O'clock, or top center position indicated, typically at the top center of the screen. This may permit the operator to view the display, and, since the orientation of the reference or indexing feature on the backshell is known to move the hand held sensor in response to indications of anomalies indicated on the screen. In free hand mode, the operator may choose to follow the shape of the defect, and effectively trace its location. While doing so the telemetry sensor may record the location relative to a known reference, and may record the time of day, to permit correlation to an operator's orally, hand-written or typed notes. To that end, it may also be that the apparatus may include a voice recorder 110 and may include a headset 111 for the operator to permit notes to be dictated oral, the display may include a keypad 112 or an electronic notepad, or both, by which the operator may record observations, those observations then being time correlated to the data recorded by the sensors on the basis of the voltages at loops 70, at the identified location. Alternatively, the operator may be provided with chalk or a grease pencil, or other suitable marker, and may trace, by hand, the region in which an anomaly has been found, and may give the anomaly a designation that may be correlated with recorded notes. Inasmuch as frequency analysis may tend to yield an indication of the depth of the defect, the display may also give a representation of defect depth, either by radial variation (i.e., the deeper the defect, the closer the representation to the center of the circle depicted on the display, or, conversely, the larger the radius of the presented output, as may be) or by colour variation, as, for example from yellow (near the surface), through orange, red and purple (for deep anomalies). Clearly, other permutations or combinations of colours could be chosen.

Further still, the apparatus may include an imaging sensor 114. The imaging sensor may be in the nature of a digital camera, and may permit a visual record to be made of the external condition of the pipe at the identified location, or to provide a correlation to external landmarks. The imaging sensor 114 may be detachable for convenience of operation, and may include a datalink to the processor, which may be wireless, or may include a cable connection 116. Apparatus 20 may also include a communications uplink. In some embodiments, the communications uplink may be a telecommunication link to a terrestrial microwave system, or may be a satellite uplink. The uplink 118 may be used to permit data collected at the inspection site of element A20 to be transmitted back to a base facility for post processing that may occur while the inspector A30 is still in the field at or near the inspection site. Apparatus 20 may also include one or more guides, or fences, 120, and apparatus for securing a fence 120 in place relative to the site to be inspected. Such an apparatus may include clamps 121. Fence 120 may be provided with a graduated scale, by which an operator may observe position and incremental displacement of hand held sensor assembly 22. The scale may include visible gradations in either British Imperial Units or Metric, or both, and may also include mechanical incremental indexing fittings 122. Fittings 122 may have the form of detents, or a rack of gear teeth, or splines, that may be engageable with the mating detent feature 46 of hand held sensor 22. As noted above, the combination of mating straight edges and a rounded detent that sits in v-notches may be employed.

As noted above, apparatus 20 may also include a plate member 28 which may be mounted at one end of chassis 24. Plate 28 may serve either or both of two purposes. First, it may function as a seat, cradle, support, accommodation, or lodgement for hand held sensor 22 when sensor 22 is not in use, as when being carried to the inspection site, for example. Secondly, plate 28 may provide, and may function as, a reference sample against which the calibration of apparatus 20, and hand held sensor 22 may be checked prior to use. It may be that, to the extent that the nature and thickness of the material of sample A22 are known, operation of hand held sensor 22 may be verified by inference against portions of the engineering structure that do not exhibit anomalous behaviour.

In operation, the magnetic flux across gap 'G' between the central pole piece and the containing peripheral wall may tend to be a predominantly radial flux. This flux, being a time varying signal, may tend to generate eddy currents in the underlying electrically conductive substrate, namely the object to be tested, structural element A20. The generated eddy currents will tend to be urged to flow in a direction perpendicular to the magnetic field by which they are induced. In a substrate that does not have flaws, those currents may tend to flow in a purely circumferential direction, and the field may tend to be concentric with the gap extending about the central pole piece. As such, the induced eddy currents may tend to generate a back EMF magnetic field, which in turn may (a) tend to oppose the main flux field; and (b) yield a voltage in each of legs 72 and 74 those voltages tending to be equal and opposite. The eddy currents may tend not to generate a voltage in each of legs 76 and 78 which are perpendicular to those eddy currents and substantially parallel to the magnetic field induced by them. The voltages generated in legs 72 and 74 by the eddy currents may tend to sum to roughly zero for a substrate that has no anomalies. In general, the value is unlikely to be precisely zero. However, the calibration or datum value may be recorded, and subtracted from the data observed to yield a net value or value referenced against the calibration balanced signal. Similarly, the radial flux of the main field induces no voltage in the radial legs, and induces equal and opposite voltages in the circumferential legs, and hence yields a signal that in the calibration state may be expected to total, in sum, zero across terminals 80 and 82. However, if there is an anomaly in structural element A20, the underlying structure will not permit the uniform circumferential electrical eddy current field to form, but rather may tend to distort that field in the region of the anomaly, as suggested in FIG. 5a in the region of arrow 146. The magnetic eddy current flux generated by this distorted field may not generate equal and opposite voltages in the various legs of loop 70, and may hence cause a non-zero voltage, or, more precisely a voltage that is divergent from the balanced datum voltage, to be observed across terminals 80 and 82.

When placed closely adjacent to object 22, the magnetic field emitted by core 52 may tend to produce a flux in gap 'G' between pole piece 54 and peripheral wall member 58. For ease of description and calculation, gap 'G' may be taken as being a circular annulus, although it might be another shape in other embodiments. The flux in gap 'G' may tend to flow radially relative to the center line axis CL.

The total energy coil and the field divergence coils both measure the characteristics of the interacting magnetic fields. The signals from the drive reference coil and the sensor coils are compared and are used to generate target distance and eddy field divergence information. The balance of the voltage induced in the inner and outer legs of each of the array of coils (i.e., loops 70) arranged about the central axis of the sensor assembly indicates the mean path of the eddy current in that section of the coil array. Cracks in the target material will cause the induced eddy current to have a path that deviates around the crack. This deviation appears as a phase and amplitude shift in the voltage signal from each sensor coil, namely each loop 70.

In general, the observation of a non-zero, or non-datum balanced, voltage in one loop 70, for example that loop indicated as 150, as compared to a zero sum voltage (or, actually, a balanced datum voltage) observed across the terminals of another loop 70, such as may be indicated as loop 152, may tend to indicate that (a) there is an anomaly in structural element A20, and (b) the anomaly is closer to loop 150 than to loop 152. Similarly, where both loops 150 and 152 indicate non-balanced voltages, the larger non-balanced voltage may tend to indicate a larger anomaly in the induced magnetic field, and a correspondingly larger anomaly. By passing sensor assembly 22 over element A20 the induced voltages may be monitored as a function of location. Numerical analysis of successive measurements may permit physical characteristics of the anomaly to be deduced to some extent. Further, by following the signal of greatest anomalous voltage, an operator may trace or map the anomaly, or at least the distorted magnetic field associated with the anomaly, and, by numerical computation, such a mapping may be made.

To the extent that structural element A20 has non-trivial depth, exciter coil 62 may be driven at more than one frequency, and may be driven in such a manner as to sweep a range of frequencies. The terms "high" and "low" frequency are relative, and may differ according to the material of structural element A20, and its thickness. All else being equal, a lower frequency exciting signal may tend to be affected by the presence of anomalies located more deeply in the structure, and a higher frequency less so. A high frequency signal may penetrate only a shallow distance, and may be subject to greatest distortion in the face of shallow anomalies. A shallow surface crack that may effectively obstruct a high frequency current, may not have the same effect on a low frequency signal. By passing magnetic flux signals of a range of frequencies through element A20, an inference of the depth and size of an anomaly may be obtained. Frequency sweeping may be done on the basis of equal arithmetic increments, or may occur on a geometric (i.e., logarithmic) basis.

It may be that some indication of the existence of an anomaly may be obtained by comparing the output of the total field sensed at drive reference coil 66 with the summed field observed at total energy reference coil 68. First, the total field value measured in coil 68 may be subtracted from the total field value measured at coil 66. When sensor assembly 22 is in close proximity to element A20, and in the case in which sensor structural element A20 is free of anomalies, these two values may sum to roughly zero (keeping in mind that some losses are to be expected). Where the sum is strongly non-zero (i.e., the magnitude of the signal measured at 68 is much less than at 66), this may indicate either that (a) sensor assembly is not near the sample element A20, or that there is a defect of significant magnitude in the sample that is preventing a large eddy current field from being generated. It may also indicate that the sample is thinner than expected in some region. A measurement at coil 68 may also tend to yield a value corresponding to the total magnetic flux seen by all of the loops 70. An anomalous voltage observed in any of those loops may then be compared to this total value.

A sensor assembly such as sensor assembly 22 may be constructed with as few as two such sector loops 70 of differing footprints, such that a differential voltage may be observed in the region of an anomaly. However, deduction of the location, shape and size of anomalies may be somewhat easier, and may perhaps be performed to a better level of accuracy or higher resolution where more than two such loops 70 are employed. The use of three loops, which may be on 120 degree sectors, or 4 loops, which may be on 90 degree sectors, or n loops, which may be on (360/n) degree sectors may improve resolution. It may be noted that the loops may overlap (i.e., 4 loops of 120 degrees of arc, on 90 degree pitch spacing) may be used, and loops that have gaps between them may be used (e.g., 12 loops of 15 degrees of arc, on 30 degree pitch spacing). Further still, it may be that two (or more) arrays of overlapping sectoral loops may be used. That is, there may be a first array of 12 loops 70, each of 30 degrees of arc, and a second array of 12 loops 70, also each of 30 degrees of arc, superimposed on the first array (assuming the number of turns of each loop to be small, the wires to be fine (i.e., or small diameter) and thus the overall coils being of small thickness in the axial direction as opposed to their extent in the radial and circumferential directions). The two arrays may be offset by 15 degrees of arc. The number of possible alternatives is large. From amongst that range of alternatives, in one embodiment there may be 16 such loops 70 of generally trapezoidal shape, formed in sectors of 22.5 degrees. The combined footprint defined by the individual regions or footprints of the segments defined by the various loops of the array, all taken together, may define a generally or substantially annular shape or region of coverage. Although mathematically convenient, and desirable from both the manufacturing and post-processing calculation perspectives, it is not necessary that the sectors all be of the same size, or that they abut precisely with neither gaps nor overlaps. The range of gap or overlap might be +/−20% of the segment size, for example, and might be expressed in terms of the angle of arc subtended by the segment. Typical sector sizes and pitch spacings may be 10, 12, 15, 18, 20, 22.5, 30, 45, 60, 72, 90 or 120 degrees. The output terminals of each of those loops 70 are connected to be polled by a signal processing unit in which the observed values may be recorded for further post processing, or may be processed immediately, in whole or in part, to provide a real-time output, or may be both stored and processed as may be. That is, there may be an initial analysis by which a coarse indication of defects may be obtained. A coarse pass may be followed by a slower or more in-depth pass, at which there may be either or both of (a) a reduction in the traverse rate, or traverse in discrete, relatively small intervals; and (b) sampling at a larger number of different frequencies, with a finer gradation of change between the various frequencies.

In one mode of operation, the operator is provided with a sensing apparatus as described, with a hand held sensing unit of appropriate size for achieving a desired depth of penetration. It may be that the desired depth of penetration is half, or less than half, the diameter of the peripheral wall of the core. The operator may input sweep parameters to the sensing apparatus related to the type of material to be inspected, and the nominal thickness of that material (assuming it to be known). The hand held sensor assembly may be checked for calibration against reference plate 28, and then placed next to a region to be surveyed, A22. The operator may have been provided with pipeline pig or other data suggesting the presence of anomalies in a particular region. The operator may establish a location reference, and may begin to sweep the structure to be inspected. The initial sweep may be a coarse sweep of a few frequencies (for example three). The sweep may involve a first sweep at one frequency, a second sweep at a second frequency, and a third sweep at a third frequency, and so on for the number of frequencies to be swept. Alternatively, the sweep may be a multi-frequency sweep in which two or more exciting frequency waves are employed at one time. That is, the sweep may involve successive observations by frequency in series, or observations taken of several frequencies in parallel (i.e., simultaneously) with the wave forms being superimposed, and the output subject to Fourier analysis to extract results for the various frequencies. Such a coarse sweep may involve four or five observations per second.

The method of operation may also include a second, or fine multi-frequency sweep of a region to be examined. The second sweep, which may be either in a series of frequencies, or in many frequencies in parallel, may include a larger number of frequencies than the first sweep, and the spread of frequencies may be on a finer gradation. For thick materials, which may require sampling at lower frequencies, each observation point may be require a sampling of 4 or 5 seconds duration.

The sweep may involve subjecting the electrically conductive object workpiece to an electromagnetic wave and generating eddy currents therein in consequence. As described above, performance of the sweep may also include providing first and second eddy current EMF detection loops, those loops having non-coincident footprints such that a voltage level observed in one such loop may differ from a voltage level observed in the other differentially according to the presence of an underlying anomaly in the adjacent object workpiece to be examined. That is, assuming each loop to have a reference voltage for a reference member having no anomalies, a difference in sector response may permit an inference to be drawn with respect to the size, location or nature of an anomaly.

Figure 5A:
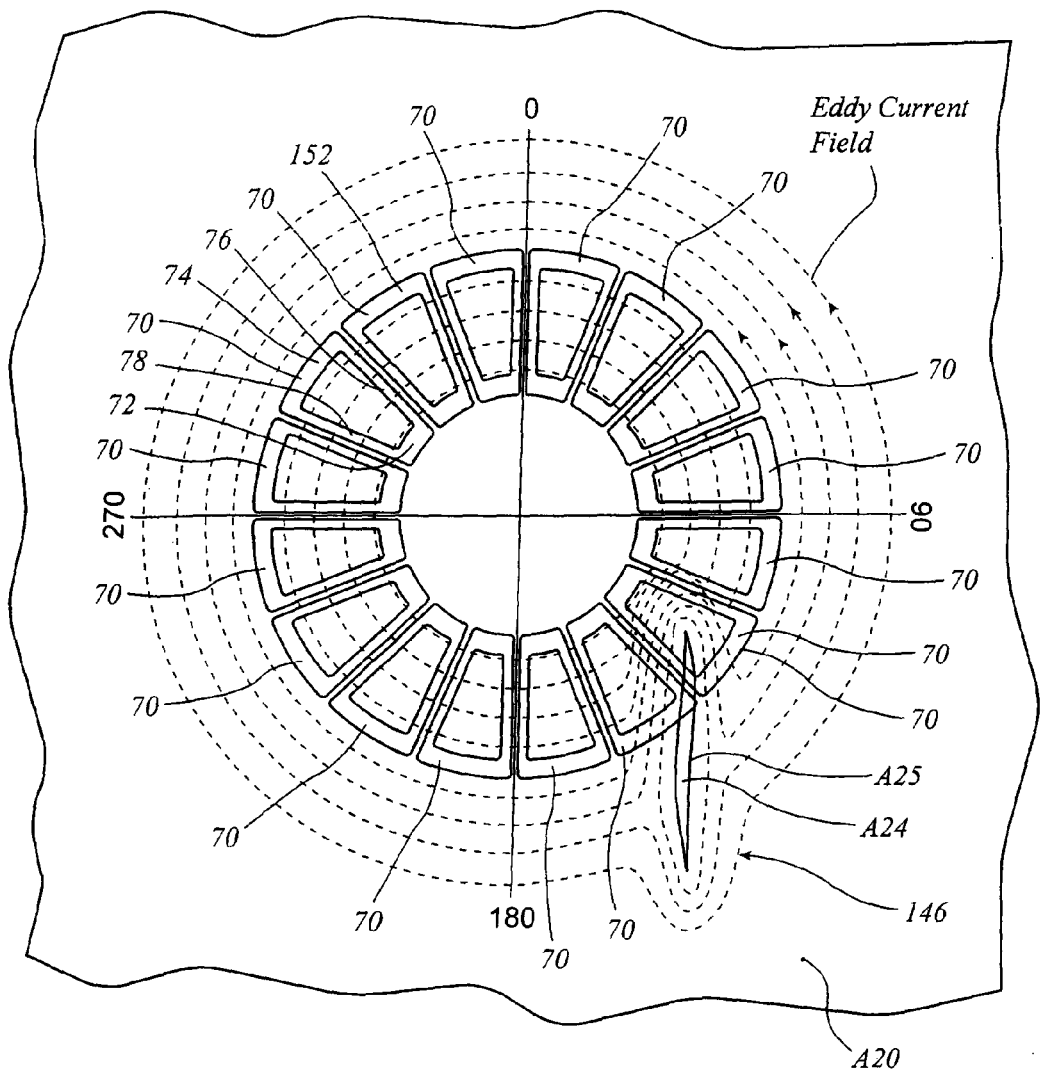
FIG. 5a shows a mapping of sectoral eddy current divergence detection elements in a plan view orientation superimposed over the object of FIG. 2 in the region of a defect, with eddy currents depicted.
Figure 5B:
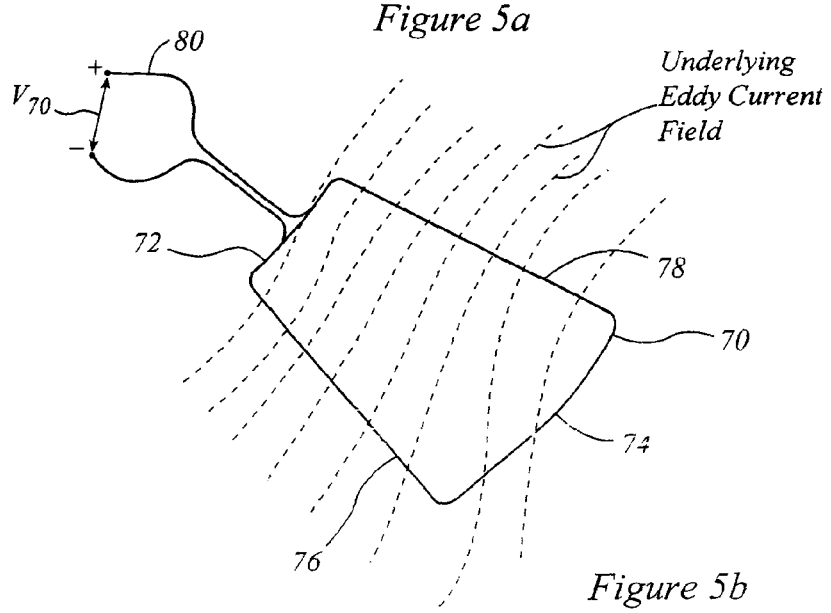
Figure 6:
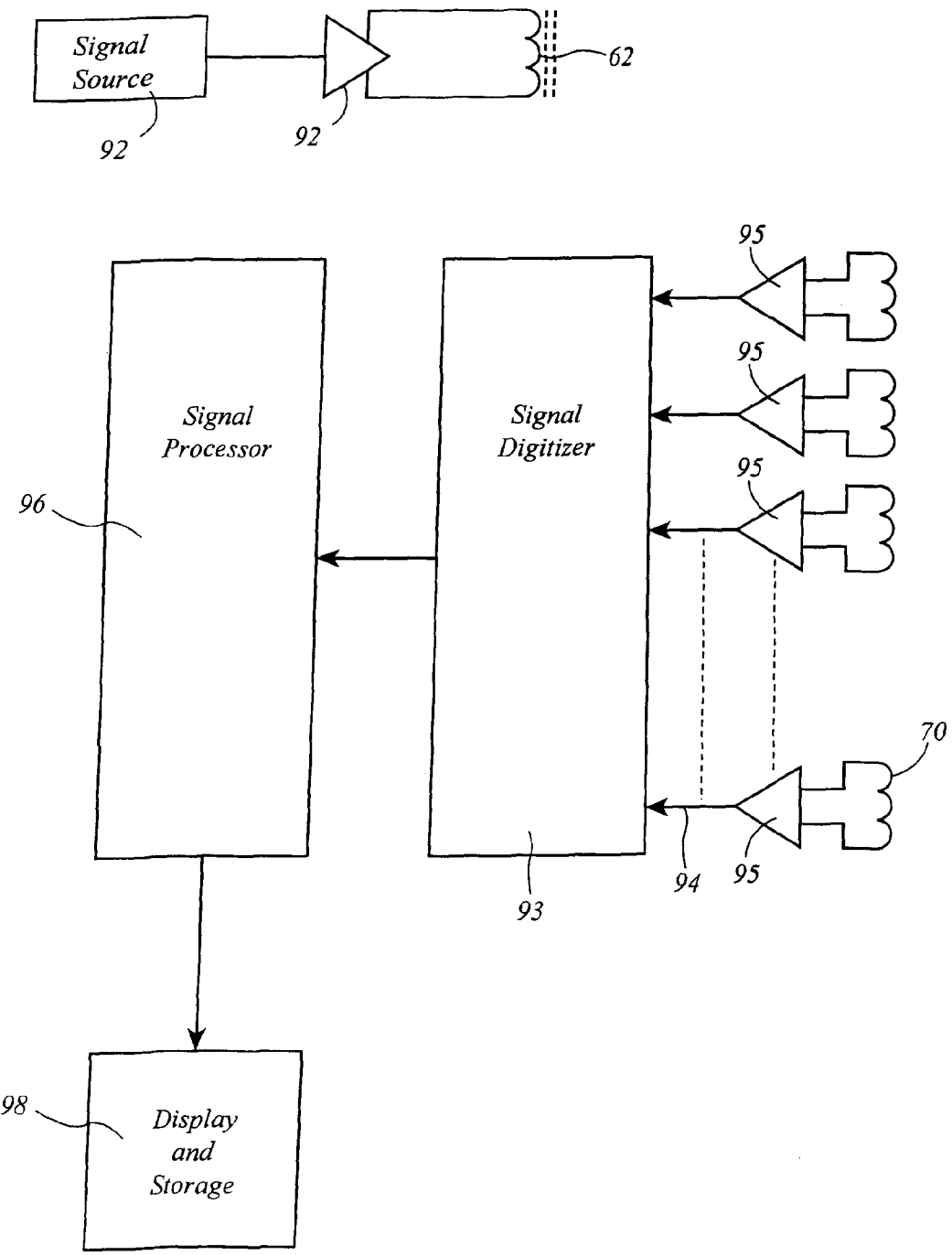
Figure 7A:
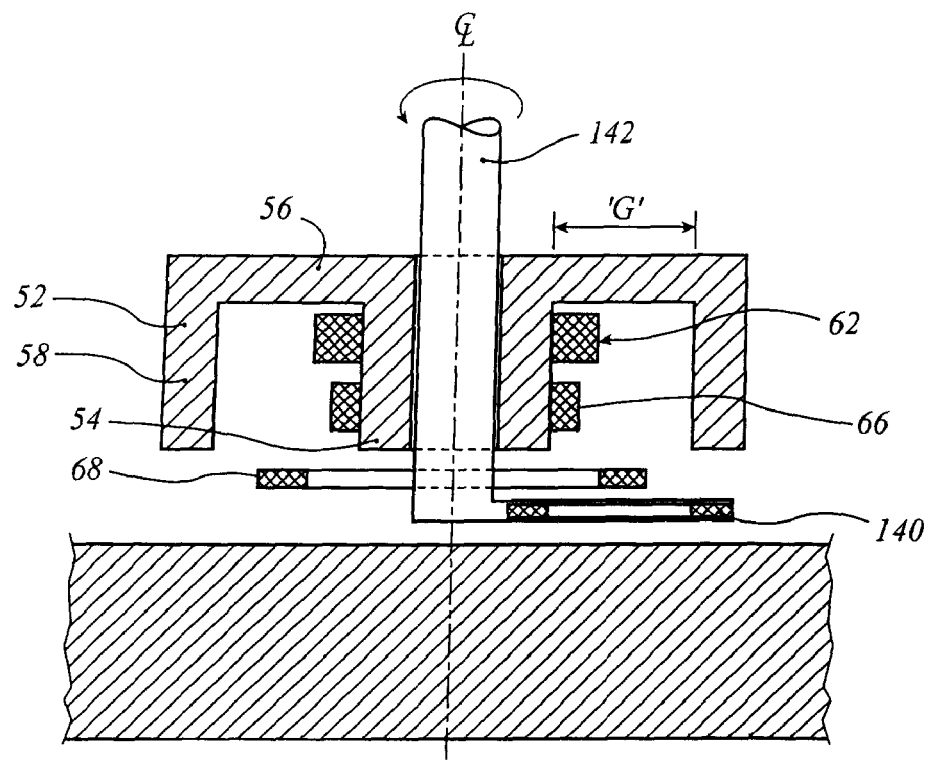
Figure 7B:
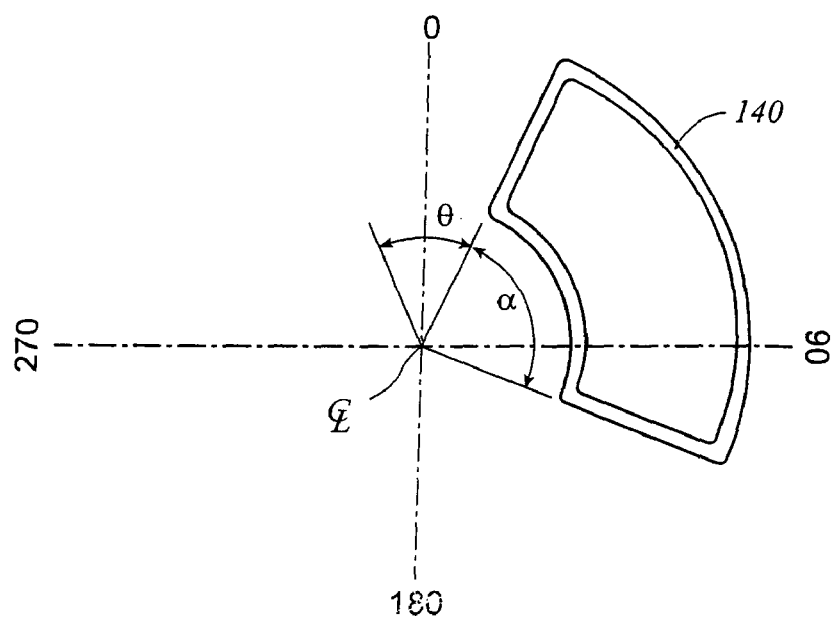
FIG. 7b shows, in plan view superimposed on a polar co-ordinate system, a configuration of an eddy current divergence sensor coil.

It may be that, in an alternate embodiment as shown in FIGS. 7a and 7b which correspond generally to the views of FIGS. 5a and 5b, respectively, (FIG. 7a being axially exaggerated for clarity) there may be a single sectoral eddy current sensing coil 70. That coil may have a footprint that is eccentric with respect to the center line axis, CL, such that a voltage observed in that coil is reflective of only a portion of the eddy current region in the gap 'G', and, to the extent that the hand held sensor can be rotated about axis CL through some incremental arc θ, or sets of arcs θ at successive steps, readings can be observed for differentiated regions of the eddy current field in gap 'G'. For example, supposing hand held sensor had only one loop 70, the set of results observed could be obtained by making a frequency sweep at one position, rotating hand held sensor 22 through an arcuate increment of 360/n degrees, making another sweep, rotating again through the arcuate increment, sampling again, and so on, for a series of n steps, until the entire annular region of gap 'G' had been sampled. Equivalently, a single loop 140 may be mounted a shaft 142 having a rotating arm 144. The arm (or disc, as may be) may rotate about axis CL, the observed eddy current signal being transmitted either wirelessly, or by slip rings, as may be convenient. Sampling may occur as the disc spins or is moved in discrete ascuate steps, each step involving an angular increment θ. A stepper motor may be used to rotate shaft 142. The arm may move in a continuous sweep, with the frequency of the angular rate of rotation being much slower than the lowest frequency being swept. Alternatively, the arm may be moved in discrete angular steps, symbolically θ, from sampling point to sampling point. Although it is convenient to assume that the angular increment corresponds to the value 360/n, and that all of the angular increments are of the same size, and where the sampling loop subtends an arc relative to the centerline CL about which the arm turns, in the most general case this need not be so. For example, in the general case illustrated in FIG. 7b, loop 140 may subtend an arc α, which may be larger or smaller than θ and the angular increments could be irregular. Assuming that the back EMF of such a monitoring coil is small, if not very small, compared to the strength of the EMF field generated by the eddy currents themselves, such that the field can be sampled without self-induced error, such a process would, eventually, result in a set of data that is the same as if n loops of the same size and shape had been arrayed about centerline CL on 360/n degrees pitch spacing, and all monitored at the same time. Similarly, in another alternate embodiment, there may be two such loops centered on different sectoral angles, and, whether subject to successive rotations or not, two such loops may yield a differential such as to provide an indication of an underlying anomaly. In the most general case, the footprints of these loops need not be of the same shape or size to produce differential data from which the presence of anomalies can be inferred by post processing calculations. As with the embodiment described above, this embodiment employs sensing circuitry that is operable to sense local variations in eddy currents in the gap of the electromagnetic driver.

While the foregoing explanation has been made in the context of a structural member A22 having a coating A22, tool 20 may also be used to find defects in structural members that do not have a coating or covering. It will also be understood that the determination of the existence of an anomaly in the back—EMF field is in relationship to what that field would be like if no anomaly were present. Therefore the shape of the sensor, the shape of the loop, the number of turns of the loops, and so on, may be somewhat arbitrary.

Figure 8A:
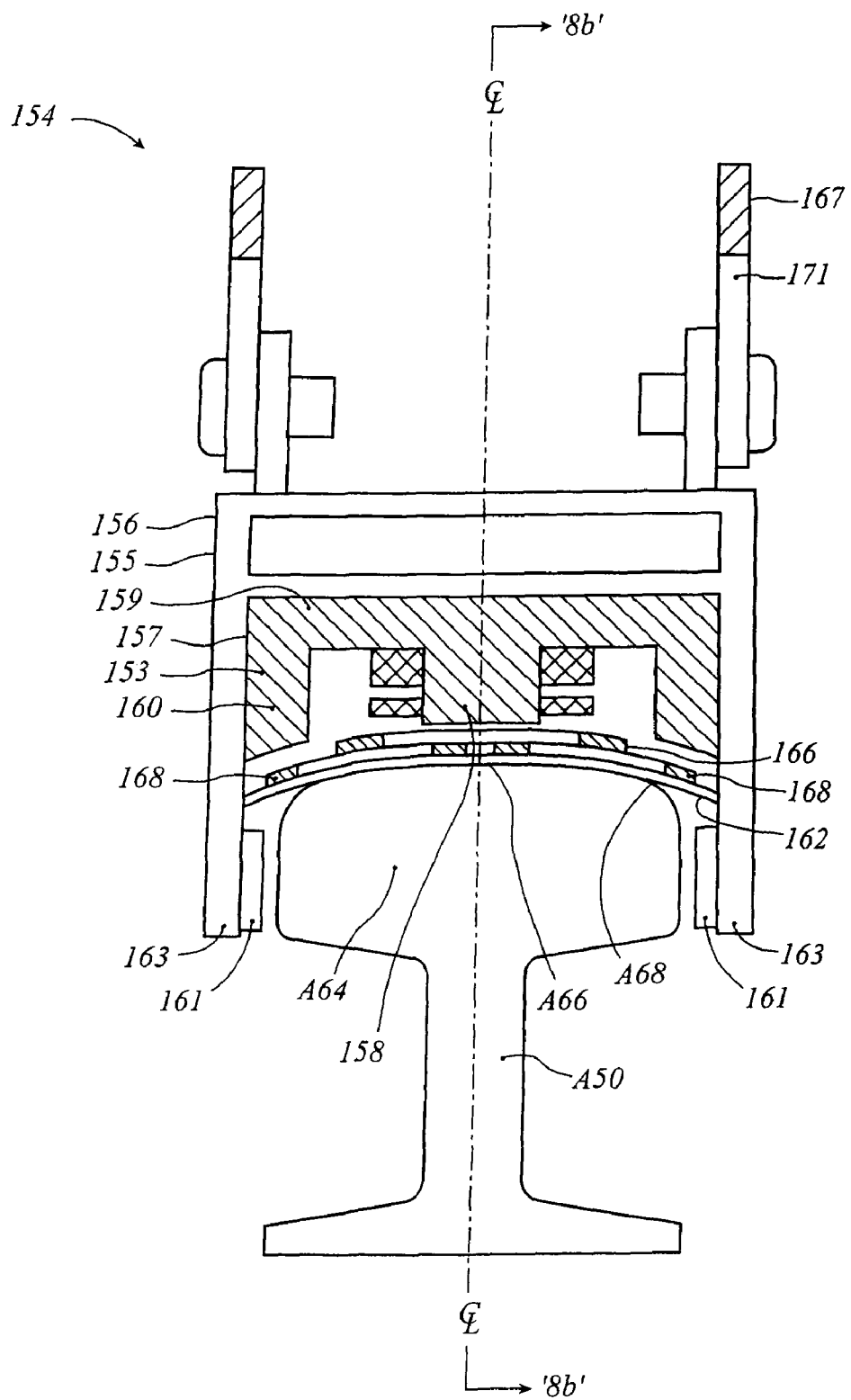
Figure 8B:
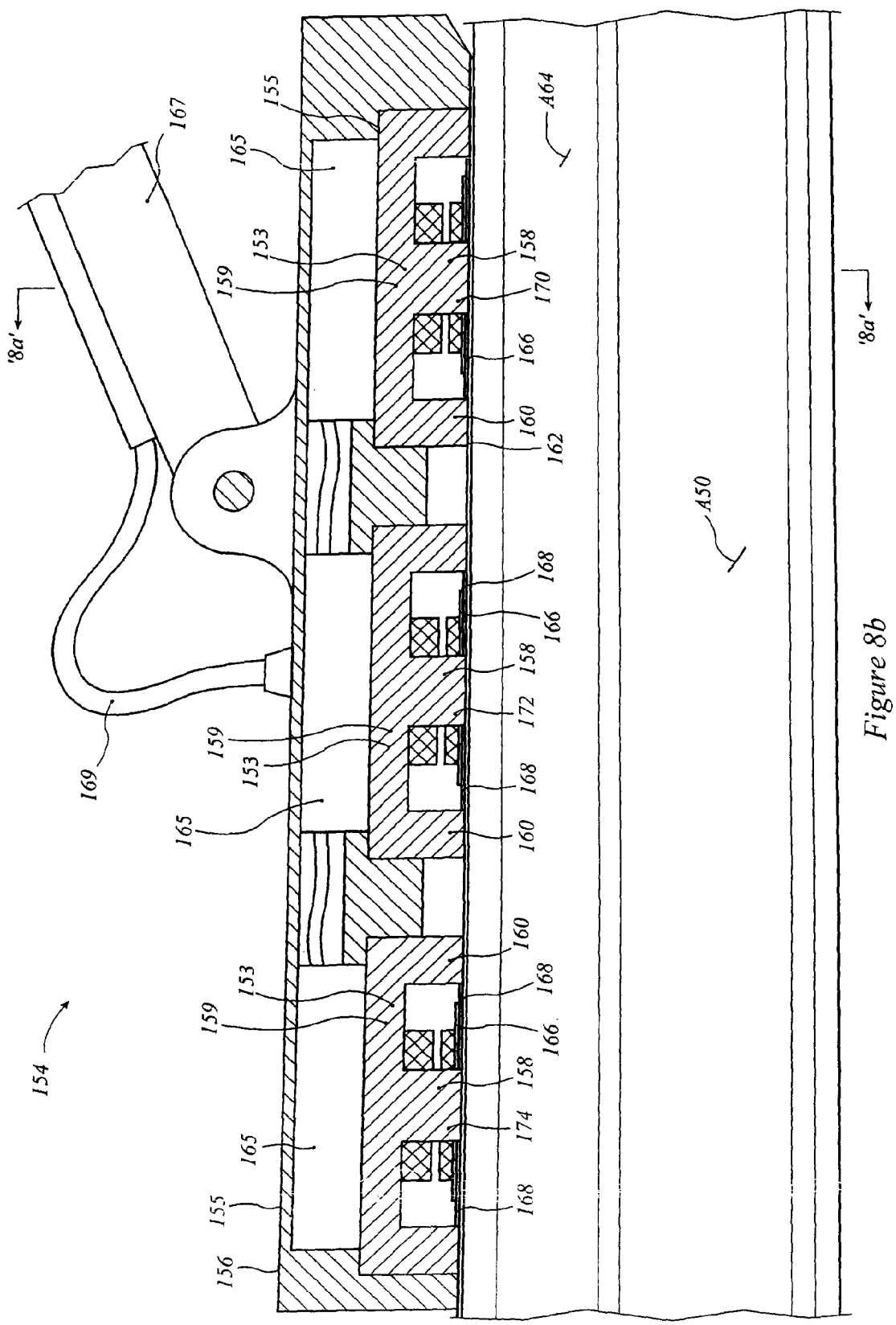

In a further embodiment, shown in FIG. 8a and FIG. 8b, it may be that a sensor is desired to detect by observed divergence of electromagnetic eddy currents anomalies in an object that either (a) is not flat, e.g., has a small radius of curvature as compared to the footprint diameter of the sensor; (b) is not a plate, such as a flanged connection in a pipe; or (c) is not necessarily of finite depth in terms of the range of effective searching frequencies to which the object is to be subject. Two particular examples are (a) sensing for eddy current field anomalies adjacent to pipe flanges in pipelines; and (b) sensing for eddy current field anomalies in rail road track rails.

Consider, for example, the case where the subject article is non-planar. For large radii of curvature, the effect of variation in lift off gap about the peripheral wall 58 may be considered small. That is, in defining terminology in this regard, and employing a cylindrical polar co-ordinate system in which the axial direction is parallel to the center line axis CL of the exciting coil and core pole piece, e.g. core pole piece 54 in the previous example, the radial direction is measured radially away from, and perpendicular to the axial direction, and the circumferential direction is mutually perpendicular to the axial and radial directions, circumferential displacements being measure from an arbitrary reference (such as, for example, the 12 O'Clock, North, or zero degree datum). It may be that when the substantially planar shoe, or sole of the shoe, e.g. plate 84 is passed across an arcuate surface, such as that of a pipeline, the axial gap between the shoe and the pipe surface may vary as a function of angular and radial position. Assuming the hand held sensor, or probe, has a substantially circular footprint and has an outer diameter of about 2 inches, this variation may be numerically manageable, either as having negligible effect or as being manageable in post processing, provided that the diameter of the pipe is at least about 5 or 6 inches or so. I.e., $d_{pipe}$ is about $2\frac{1}{2} \times d_{sensor}$, or greater.

Where the variation begins to become significant, perhaps in the range of $d_{pipe}/d_{sensor}$ being 3:1 or less, for example as a starting point, if not 4:1 or less, it may be either desirable or convenient to use a non-planar tool head on the sensor. Consider, for example, a relatively sharply curved surface, such as a small diameter pipe or the head of a rail road track rail A50, such as the example shown in FIGS. 8a and 8b. In this instance the hand held or otherwise relatively portable sensor 154 may be provided with a sole, or sole plate assembly, or shoe 156 that has a housing 155. Inside housing 155 is an accommodation 157. A magnetically permeable core 153 is mounted in accommodation 157. Core 153 is substantially similar to core 54 described above. Core 153 has a magnetically permeable pole piece 158, a backing plate 159, a peripheral wall 160. At the sensing end of the unit, the distal ends of pole piece 158 and peripheral wall 160, and the non-participating cover 162 are shaped to conform to the contour of the surface of the target object to be examined, e.g., the head of the rail. While that contour may be formed on a cylindrical surface of constant radius of curvature, in the most general case that need not be so. For example, consider the bull head A64 of FIG. 8a. The top central portion of the rail, at A66, may be formed on a curve of a first radius of curvature, and the adjacent shoulders, as at A68, may be formed on a curve of another, usually smaller, radius of curvature. The total energy reference coil 166 and the loops 168 of the eddy current divergence sensors in the eddy current sensing array are also shaped to conform to bull head A64. In this instance, the hand held sensor may be used for sampling traverses along a single degree of freedom, namely translation parallel to the long axis of the pipe or rail, without substantial departure from that direction. (i.e., as compared to two degree of freedom translation when a substantially planar probe head is employed). Amplification of the raw data voltage signals and conversion of those analogue signals to a digital form may occur in electronic modules 165. Housing 155 may include downwardly depending members 163, such as may be termed skirts, or guides, or sideplates, which are spaced apart in a manner permitting members 163 to straddle bullhead A64 of rail A50. The inside face of members 163 may include a wear strip 161, which may be a consumable item, and which may be made of, or have a coating of, a low friction material. Depending members 163 may tend to urge sensor 154 to follow the rail. Similarly, the towing link may be mounted on a relatively wide based clevis 171, and may tend to aid in maintaining the centerline axis CL of the sensor parallel to, and substantially co-planar with the vertical centerline of the rail.

It may be that in an application such as that of FIGS. 8a and 8b, some of the sectoral readings from loops 168, or such analogous loops as may be employed, may have a non-zero summing at the reference, or calibration, reading in material that is free of anomalies in the regions relevant to testing. The reference, or non-anomalous datum value for eddy current divergence need not be zero. In general, whether in the embodiment of FIG. 4 or the embodiment of FIG. 8a, or some other, the sensor serves to permit observation of deviation away from the datum reading even if that datum is non zero. That is, while the datum may typically be a zero voltage value, it need not necessarily be. Divergence from the datum, even at a single data point may suggest the presence of a field anomaly for further examination. A multiplicity of readings may again be taken at known positions. Data gathered at those positions may then be subjected to post processing to permit extraction of inferred size and location information of an observed anomaly.

It may be that in the case of a rail road track, or other similar object, a probe or sensing apparatus may be trailed over the object in a running manner, e.g., at some relatively constant traverse speed. The shoe 156 may have a connecting rod, or link 167 by which shoe 156 may be pulled by an instrumented car, in which post processing and data collection may proceed while sampling is taking place. A data transfer cable 169 may be provided to permit power signals to be delivered to shoe 156, and observed data to be retrieved for post processing. It may be taken that the location at which the sampling is undertaken may be recorded by telemetry equipment in the instrumented rail road car, or other vehicle, in which the power supply and post processing equipment, or data recording equipment are located. It one embodiment it may be that some signal processing may occur in electronic units 165, or that some data recording may occur in electronic unit 165. However, it may be more convenient for such processing or recording to occur in the main unit, analogous to chassis 24, in the towing vehicle.

Shoe 156 may have a relatively long and thin aspect ratio corresponding to the object to be examined, and may include more than one sampling head, such as heads 170, 172 and 174. These heads may each operate over several frequencies, with different frequency ranges such that a larger overall range or number of frequencies are sampled in each pass, or that multiple samples may be taken at each data point as the successive heads pass over. This may tend to permit a higher resolution analysis of the resulting data. The discussion above has assumed a finite wall thickness, and a probe focussing peripheral wall diameter that is greater, usually more than double, the wall thickness to be observed. For a steel rail, the frequency range suitable for observing anomalies as deep as ½ inch from the surface may extend to a low frequency of the order of 5 to 10 Hz. This may imply a relatively slow traverse rate. However, to the extent that the region of interest for failure crack initiation may be relatively close to the surface of the object, such as in the 1/16 inch depth closest to the surface, it may be that sampling to a non-through thickness depth may detect anomalies of interest. That is, sampling may occur over a range of frequencies whose effective sampling depth may be less than the range required to sample the full depth. In the case of the rail, the effective sampling depth may be ¼ inch, and the range of frequencies swept may have a low end frequency of 50 to 100 Hz, and a high end frequency of 20 kHz., with a number of swept frequencies that is in the range of 3 to 30, e.g., 3 frequencies for a fast sweep, and 12 to 20 frequencies, or more, for a slow, in-depth sweep. The towing rate of sensor 154 may be a function of desired depth of observation, and, in some embodiments, may be as much as 20 m.p.h or more.

Figure 9:
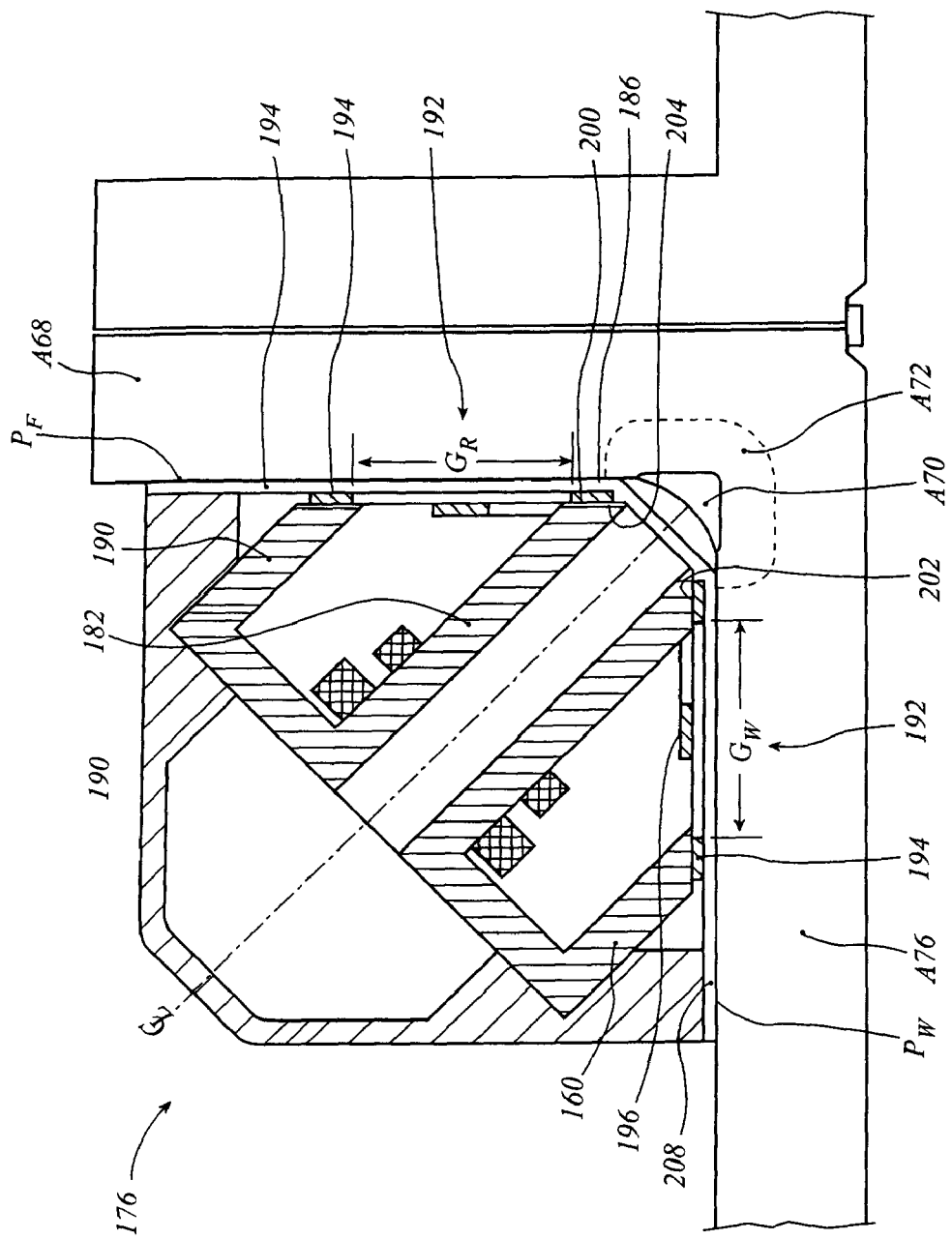
FIG. 9 shows a central cross section of another embodiment of anomaly detection apparatus, place in the angle between a pipe wall and a pipe coupling flange.

Another type of sampling may occur where the object to be examined may be as shown in FIG. 9a. FIG. 9a shows a cross-section of a pipe flange A68 (hatching omitted for clarity). Flaws and anomalies may often be present at locations such as the welds formed in continuous rail, or in the welds A70 or in the adjacent heat affected zone A72 at welded flanges in pipes, or at joins between plates in welded structures more generally, be they ships, rail road cars, or other structure. In this instance, the sensing probe assembly 176, which, again, may be a hand held assembly, may include a specially shaped shoe 180 that includes a core 178. The high permeability central core 178 may be substantially as before. In FIG. 9a, a sensor shoe 180 includes a core pole piece 182 that has a distal end 184 having an angled orientation. A high permeability peripheral focussing wall 190 extends about a central pole piece 182, leaving a gap region 192 that includes portions $G_F$ of flange A68 and portions $G_W$ of the cylindrical pipe wall A76 adjacent to the flange A68. Eddy current divergence sensors 194 are again arranged to observe eddy currents in the gap, as is the total eddy current coil 196. Total current coil 196 is bent to follow the corner, inside cover plate 186. It may be that pole piece 182 has a cylindrical core 198 that has been mitred as at 200 and 202 to give a chisel edge or apex 204 at the root of the flange to pipe weld. Core 198 may then have two side or face portions, 206, 208 for placement adjacent portions $G_F$ and $G_W$ of respectively. If viewed parallel to the centerline axis CL, the projected image of core 178, including pole piece 182 and peripheral focussing wall 190, may have a circular appearance, not unlike that of the corresponding central pole piece 54 and annular wall 58 of core 52. In this embodiment, face portions 206 and 208 may have generally semi-elliptically shaped footprints relative to portions $G_F$ and $G_W$. Alternatively, the chamfered face portions 206 and 208 may be given a semi-circular shape, or such other shape as may be selected. The apex 204 may be radiused or chamfered to clear an existing radius of the weld metal fillet at the root (i.e., the radially innermost termination) of the flange. This probe may be traversed in circumferential steps about the pipe, and data recorded and analysed accordingly. It may be noted, again, that in this circumstance, the reference or calibration reading of various ones of the eddy current divergence sensor loops 202 may be non-zero, and the recording of data and post processing may proceed on the basis of evaluating divergence from that standard datum. Although it may be convenient for the angle of inclination to bisect the angle at which the flange meets the pipe wall, which may be the included angle between cover plate flange and wall opposing portions 206 and 208 respectively (i.e., typically 90 degrees, the bisector being at 45 degrees), other angles may be used. Similarly, while it may be convenient for the centerline of the central pole piece to intersect the locus of intersection of the flange and the pipe wall at their root. It may be that the central axis of core 198 may be positioned such that, in operation it does not intersect the weld fillet, but rather, that it lies offset from the locus of intersection of the planes $P_F$ and $P_W$ defined by the flange and wall face portions 206, 208, respectively, of the shoe, e.g., of the wear plate or cover plate 186. Divergence sensors 194 may also be formed to follow the contour of cover plate 186.

In the case of welds in continuously welded rail of a rail road track, the core may include a horse-shoe shaped, high permeability wound core, between two similarly horse-shoe shaped focussing walls, and rather than being moved parallel to the weld, as in the pipe flange example, the horse-shoe shaped sensor may be moved along the rail perpendicular to the weld, in very small repetitive increments. Such a probe may include two portions and a backing, or web portion, and, somewhat like clamp, the sensor may be placed over the rail and one portion advanced using a screw. Once positioned, the movable member may be clamped tightly in position to make a good magnetic circuit.

Figure 10A:
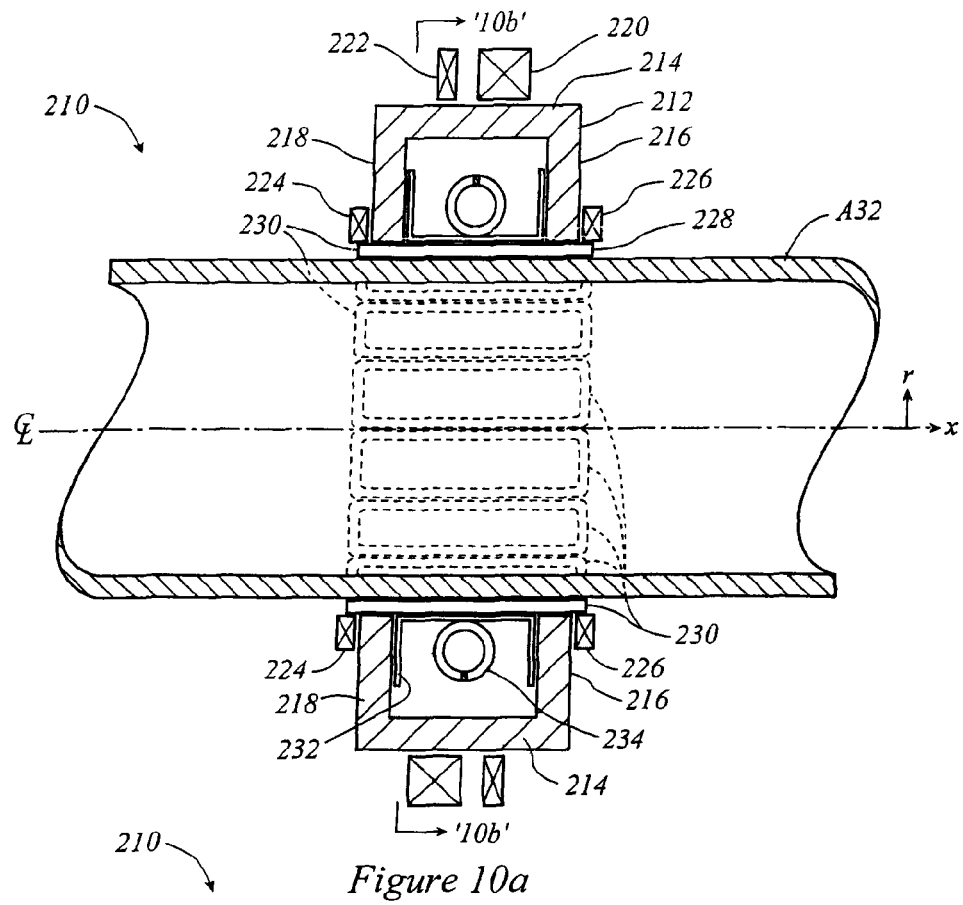
FIG. 10a shows a longitudinal cross-sectional view of another embodiment of anomaly detection apparatus mounted about a pipe.
Figure 10B:
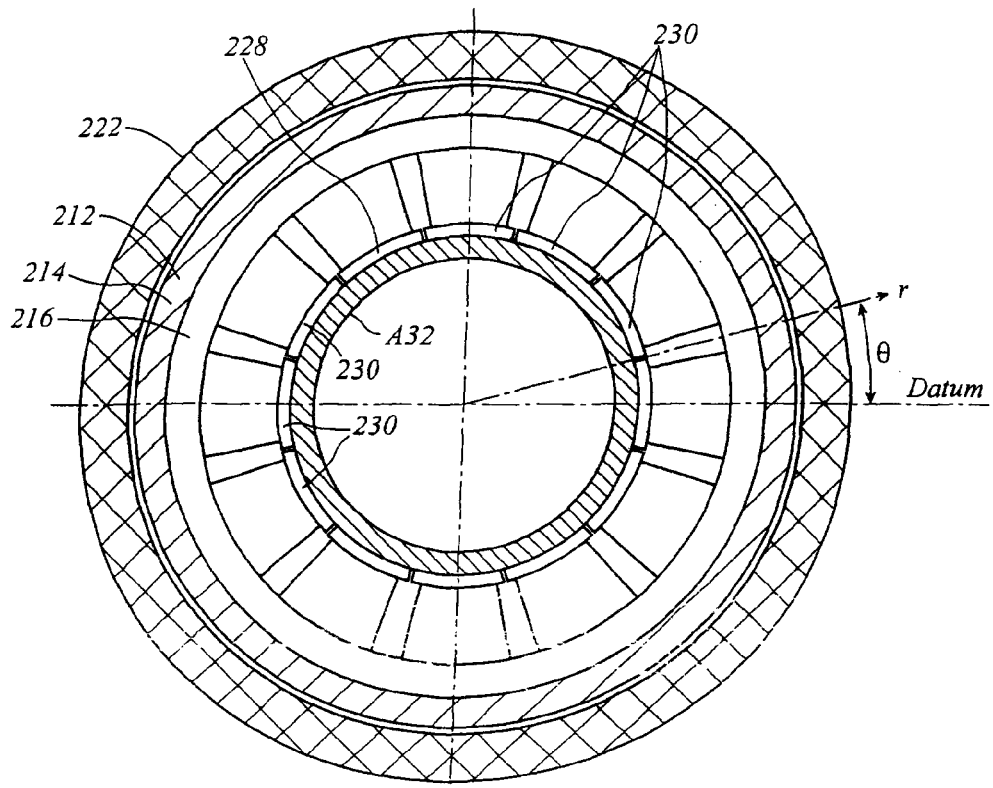

In the embodiment of FIGS. 10*a* and 10*b* there is a generally annular embodiment of anomaly detector 210 through which a hollow pipe A32 of corresponding diameter may be passed. In this embodiment there is a core 212 of high magnetic permeability. Core 212 has a channel like cross-section, as illustrated, the channel having a back or web 214 in the form of an axially extending, circumferentially running wall, and a pair of spaced apart legs 216 and 218 in the form of radially inwardly extending, circumferentially running annuli.

An exciter coil 220 and a drive reference coil 222 extend circumferentially about web 214. There are circumferentially extending total energy reference coils 224 and 226 axially adjacent the toes of legs 216 and 218 respectively, being axially outside, and bracketing, those legs. The voltages sensed in these coils are additive. An array 228 in the form of a belt of eddy current divergence sensing loops 230 girdles the pipe inside the radially inner extremities of legs 216 and 218. In operation, time varying forcing currents in the exciter coil impart a correspondingly time varying signal to the magnetic core 212, and to the pipe wall in the region between legs 216 and 218. This axial time-varying magnetic field in the pipe wall may tend to generate circumferentially flowing eddy currents, which in turn have an associated back-EMF that produces an observable voltage in each of loops 230. The variation of these sensed voltages from a datum value is sensed, as a above, and processing of the voltage data so obtained may permit inferences to be made, typically by means of digital processing, about the size, shape, and location of anomalies in the pipe wall. As above, the time varying signals may include wavetrains of several different frequencies, and the repeated sampling at successive axial positions along the pipe, as discussed above. The radially extending sidewalls of the magnetically permeable core 212 may include radially movable portions, segments, or sections 232 to accommodate, or give tolerance for, a range of pipe or bar sizes. Sections 232 may have a cross-section in the form of a channel nested inside (,or bracketing outside) core 212, and may have loops 230 mounted to the back thereof. Sections 230 may be urged radially inwardly by a biasing member, such as a non-ferromagnetic, non-electrically conductive resilient band or spring, such as a circumferentially running plastic or other spring 234. Loops 230 may be correspondingly radially movable to some extent, and, to facilitate that motion, there may be gaps between loops 230 at the largest radius, or one leg of each loop may be mounted to ride up upon, and to overlap, the next adjacent loop when the pipe radius is reduced. The face of each loop 230 may be encapsulated in a protective plastic coating, or may have a wear skin of either plastic or other non-participating material. Where skin plates are employed, their edge may overlap to permit radial motion of loops 230.

Figure 11B:
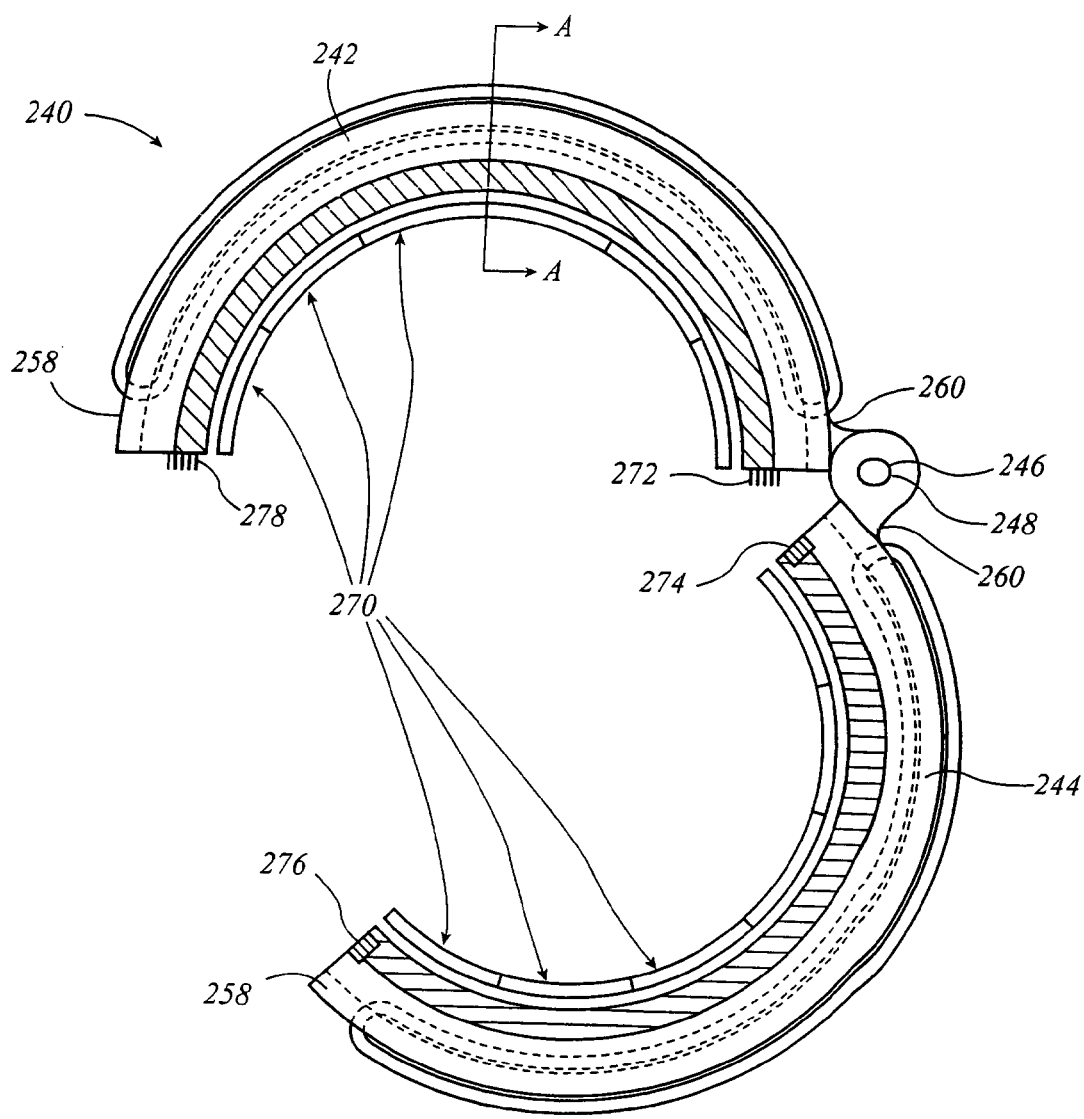
FIG. 11b shows a cross-section of the apparatus of FIG. 11a on section '11b-11b'.
Figure 11A:
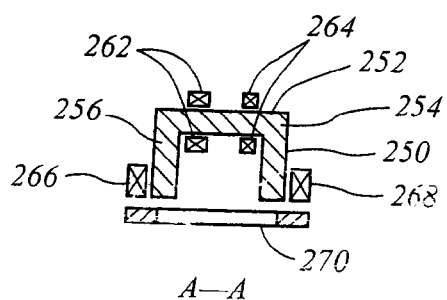

It may be convenient to be able to open a ring, or peripheral anomaly detection device, perhaps generally similar to that of FIGS. 10*a* and 10*b*, such that it may be placed about an intermediate portion of the object to be examined A32 where there is no convenient end at which the detection apparatus can be placed on the object. The embodiment of FIGS. 11*a* and 11*b* shows an anomaly detection apparatus 240 for placement about the periphery of, for example, object A32. In this instance, apparatus 240 has two portions, or wings, or sectors, 242, 244 that are connected at a flexible connection 246, which may be a hinge 248. While sectors 242 and 244 may have the form of sectors of a circle, which sectors may approximate, for example, semi-circles, they could be of a different shape such as may tend to conform to the outer peripheral shape of the object to be examined. For example, in alternate embodiments, apparatus 240 may include multiple segments hinged together in a manner analogous to tread sections of a bulldozer track, with additional links being added or subtracted as appropriate for the size and shape of the object to be examined. Where a large number of segments is employed, the face of each segment may tend to approximate a flat sector, or chord.

In reference to the embodiment of FIGS. 11*a* and 11*b*, each segment 242 or 244 may include a high magnetic permeability core member 250, which may have a generally U-shaped cross-section, as seen in FIG. 11*b*, having a circumferentially extending back or web, 252, and radially extending legs 254, 256. Web 252 may be notched at either end, as at 258, 260 to permit the windings of an exciter coil 262 and a drive reference coil 264 to be wound thereabout. Each segment may be provided with its own exciter and reference coils, and the set of exciter coils of the various segments may be controlled electronically to operate together to produce co-ordinated time varying magnetic fields that may tend to generate eddy currents in object A32 in a manner that may approximate that of a continuous circular core. Again, the approximation need not be perfect, since the resultant eddy current divergence is measured against a datum value for the apparatus. That is, in a multi-segment device, it may be that less than all of the segments include exciter coils, provided that enough do to produce eddy currents in the region of object A32 to be observed, and therefore a back EMF to be monitored and compared to a datum value, whatever that datum value may be. Apparatus 240 may also include a pair of first and second axially spaced apart total energy reference coils 266, 268, located to either side of legs 254, 256 respectively, such that core member 250 is bracketed, and the sum of the voltages measured in coils 266, 268 may tend to correlate to the magnitude of the total eddy current field induced by exciter coils 262 in object A32. Apparatus 240 may also include an array of eddy current divergence monitoring elements, or sensors, in the nature of sensing loops 270 whose structure and function are analogous to, and possibly identically to, loops 70 and 230 noted above. The operation of apparatus is fundamentally similar to that of the other anomaly detection apparatus described above, involving multi-frequency sweeping, and incremental changes in position. However, apparatus 240 may be opened, as shown in FIG. 11b to permit placement about object A32, and closed in place. When closed, the corresponding mating contacts, 272, 274, 276 and 278 of total energy reference coils 266 and 268, which are multi-pin contacts in which there are pairs of mating contacts corresponding to each turn of each coil, are brought together and engaged to complete the turns of those coils. The faces of the loops 270 may be provided with a protective coating or skin as a wear shield.

In each of the embodiments described, the core has included either a central pole piece and a co-operating magnetically permeable peripheral wall (as in the embodiments of FIGS. 4, 7a, and 8a) or a pair of circumferential co-operating legs (in the embodiments of FIGS. 10a and 11a). In each case, the pole piece and the peripheral wall, and the pairs of legs, act, in effect as poles of an electro-magnet driven by the exciter coil to emit a time varying magnetic flux field. It may be possible to mount an array of sensors about the core, without a peripheral wall in the first instance; or to use a single circumferential annular leg and sensors in the second instance, in both cases relying on a return magnetic field through the surrounding medium, which may be air, water oil, or another relatively low magnetic permeability substance. This may tend to increase the power requirement for the exciter coil, and may not necessarily improve performance.

The raw data may tend to have a relatively coarse initial presentation. More advanced data processing can occur on either the hand unit, if equipped with a suitable processor and software, or the data can be reprocessed later by another computer application, such as might be at a central facility, the recorded data having being transmitted to that facility. The more advanced processing may be similar in nature to magnetic resonance imaging post processing, such as may permit a relatively higher resolution observation to be made.

Various embodiments of the invention have been described in detail. Since changes in and or additions to the above-described best mode may be made without departing from the nature, spirit or scope of the invention, the invention is not to be limited to those details but only by the appended claims.

What is claimed is:

1. A portable anomaly detection apparatus for inspecting an electrically conductive object, the anomaly detection apparatus comprising:
   an electromagnetic field emitter operable to pass a time varying magnetic flux field through at least a portion of the electrically conductive object, and thereby to generate an electrical eddy current field in the electrically conductive object, said electromagnetic field emitter including a magnetic flux focusing core;
   eddy current monitoring circuitry operable to survey at least first and second portions of the eddy current field, the first and second portions being non-coterminous;
   said eddy current monitoring circuitry including a first eddy field divergence sensor coil operable directly to sense eddy field divergence in the electrically conductive object; and
   signal processing apparatus connected to said eddy current monitoring circuitry, said signal processing apparatus being operable to compare data received from said eddy current monitoring circuitry observed at said first and second portions of the eddy current field.

2. The portable anomaly detection apparatus of claim 1 wherein said first eddy field divergence sensor coil has first and second legs extending radially relative to said core, and third and fourth legs extending on a circumferential arc relative to said core, said third leg extending circumferentially relative to said core at a closer radial distance to said core than said fourth leg.

3. The portable anomaly detection apparatus of claim 1 wherein said first sensing member overlaps said second sensing member.

4. A mobile anomaly detector operable to survey an electrically conductive object, said anomaly detector comprising:
   a shoe, said shoe having a sole for engagement with the object;
   an electromagnetic field emitter mounted within said shoe;
   said electromagnetic field emitter including a magnetic flux focusing core;
   said magnetic flux focusing core having first and second soles at said sole, said poles being spaced apart by a gap;
   a power source connected to drive said emitter, said power source being operable at a plurality of frequencies;
   said emitter being operable to induce an eddy current field in the object when said sole is placed adjacent thereto;
   a plurality of eddy current sensors arrayed adjacent said electromagnetic field emitter, members of said plurality of eddy current sensors including eddy current field divergence sensor coils, each of said eddy current field divergence sensor coils being operable to sense directly eddy field differential induced in the electrically conductive object, each of said eddy current field divergence sensor coils being located to monitor a different portion of the eddy current field at said sole adjacent to said electromagnetic field emitter; and
   at least one of (a) a recorder operable to store recording data from said eddy current sensors for subsequent signal processing operations; and (b) a processor operable to interpret data obtained from said eddy current sensors.

5. The mobile anomaly detector of claim 4 wherein said sole has a profile constraining said detector to a single degree of freedom in translation, and one of:
   (a) said anomaly detector includes a plurality of said emitters;
   (b) said anomaly detector includes a plurality of said electromagnetic field emitters, and said sole has a profile conforming to a rail road track rail; and
   (c) said anomaly detector includes a plurality of said electromagnetic field emitters, and said plurality of electromagnetic field emitters includes at least a first emitter and a second emitter, said first and second emitters being movable relative to one another to permit said mobile anomaly detector to girdle the electrically conductive object.

6. The mobile anomaly detector of claim 4 wherein each of said eddy current field divergence sensor coils has first and second legs extending radially relative to said core, and third and fourth legs extending on a circumferential arc relative to said core, said third leg extending circumferentially relative to said core at a closer radial distance to said core than said fourth leg.

7. The mobile anomaly detector of claim 4 wherein one of said sensor coils overlaps one other of said sensors coils.

8. A hand portable eddy field anomaly detector for use in detecting anomalies in an electrically conductive object, said eddy field anomaly detector comprising:
   a magnetic field emitter operable to induce an eddy current field in an adjacent electrically conductive object to be examined;
   said magnetic field emitter including a magnetic flux focusing core;
   said magnetic flux focusing core having first and second poles for placement, in use, next to the electrically conductive object, said first and second poles being separated by a gap; sensing apparatus operable, while said anomaly detector is in one location, to sample, at first and second sensing regions of said gap, back EMF of the eddy current field;

said sensing apparatus operable to sample at said first sensing region including a first eddy field divergence sensor coil operable to sense directly eddy field differential in the electrically conductive object;

said first sensing region being different from said second sensing region; at least one of
- (a) a recorder operable to store data observed with respect to said first and second sensing regions; and
- (b) a signal processor operable to compare at least one of
  - (i) data observed with respect to said first sensing region and data observed with respect to said second sensing region; and
  - (ii) data observed with respect to at least one of said first and second sensing regions and a reference datum; and said first and second sensing regions satisfying at least one condition selected from the set of conditions consisting of
- (a) said first sensing region includes at least a portion not covered by said second sensing region, and said first and second sensing regions are non-concentric;
- (b) said first sensing region includes at least a portion not covered by said second sensing region, and said second sensing region includes at least another portion not covered by said first sensing region; and
- (c) said first and second sensing regions are non-concentric and at least one of said first and second sensing regions is eccentric relative to said magnetic field emitter. field emitter.

9. The hand portable eddy field anomaly detector of claim 8 wherein said sensing apparatus includes at least one of:
   - (a) an array of discrete sensors each having a different footprint;
   - (b) an array of discrete sensors each having a different footprint, said array of discrete sensors extending in a substantially annular pattern;
   - (c) an array of discrete sensors each having a different footprint, said array of discrete sensors including a plurality of said discrete sensors defining segments of a substantially annular footprint;
   - (d) an array of discrete sensors each having a different footprint, and said array of discrete sensors includes a plurality of said discrete sensors defining n segments about a central axis, said n segments being spaced on an angular pitch of 360/n degrees about said central axis;
   - (e) an array of discrete sensors each having a different footprint, and said array of discrete sensors includes a plurality of said discrete sensors defining n segments about a central axis, said n segments each subtending an angular arc of 360/n degrees +/−20%;
   - (f) a movable sensor locatable in a plurality of different sampling positions while anomaly detector remains in one place; and
   - (g) a movable sensor locatable in a plurality of different sampling positions while said anomaly detector remains in one place, said magnetic field emitter includes a magnetically permeable core having a centerline axis, and said movable sensor is angularly displaceable on an arc centered on said centerline axis.

10. The hand portable eddy field anomaly detector of claim 8 wherein said anomaly detector includes one of:
    - (a) a magnetically permeable core having a pole piece and a co-operating peripheral wall spaced from said pole piece; and
    - (b) a magnetically permeable core having a pole piece and a co-operating peripheral wall spaced from said pole piece, and said anomaly detector has a foot for placement against the object to be examined, and said foot is selected from the set of feet consisting of
      - a substantially planar base;
      - (ii) a chamfered base;
      - (iii) a chamfered base that includes a first portion and a second portion, each of the first and second portions of said foot including members of said sensing apparatus, and said first and second portions lying to either side of said chamfer;
      - (iv) a base having a contoured profile;
      - (v) a base having a profile defining a portion of a cylindrical surface; and
      - (vi) a base having a profile defining a portion of a circular cylindrical surface.

11. The hand portable eddy field anomaly detector of claim 8 comprising a hand held sensing module for passing next to the object to be examined, and a display, and one of:
    - (a) a processor operable to present anomaly identification indicia on said display;
    - (b) a processor operable to present anomaly identification indicia on said display, and said display includes an anomaly depth indicator;
    - (c) a processor operable to present anomaly identification indicia on said display, and said display includes an anomaly position indicator; and
    - (d) a processor operable to present anomaly identification indicia on said display, and said display includes an anomaly direction indicator.

12. The hand portable eddy field anomaly detector of claim 8 further comprising any of: a photographic recording medium; an audio recording medium; telemetry apparatus; and incremental change of position apparatus.

13. The hand portable eddy field anomaly detector of claim 8 wherein said anomaly detector apparatus comprises a chassis having a carrying handle, a power supply mounted to the chassis, a display mounted to the chassis, and a removable hand sensor.

14. The hand portable eddy field anomaly detector of claim 8 further comprising any one of:
    - (a) a controller operable to drive said magnetic field emitter at more than one frequency; and
    - (b) a controller operable to drive said magnetic field emitter at more than one frequency, said controller being operable to drive said magnetic field emitter at a plurality of frequencies simultaneously.

15. The hand portable eddy field anomaly detector of claim 8 wherein said apparatus includes any of:
    - (a) a sensor mounted to measure total emitted magnetic flux from said magnetic fieldemitter;
    - (b) a sensor located to monitor total eddy current back EMF; and
    - (c) a sensor mounted to measure total emitted magnetic flux from said magnetic fieldemitter, a further sensor located to monitor total eddy current back EMF; and a processor operable to compare total emitted magnetic flux to total eddy current back EMF.

16. The hand portable eddy field anomaly detector of claim 8 wherein one of:
  (a) said anomaly detector weighs up to 20 lbs.; and
  (b) said anomaly detector has a sensing module for passing next to object to be examined, and said sensing module weighs up to 5 lbs.

17. The hand portable eddy field anomaly detector of claim 8 wherein said first eddy field divergence sensor coil has first and second legs extending radially relative to said core, and third and fourth legs extending on a circumferential arc relative to said core, said third leg extending circumferentially relative to said core at a closer radial distance to said core than said fourth leg.

18. The hand portable eddy field anomaly detector of claim 8 wherein the detector includes a second eddy field divergence sensor coil operable to sense directly eddy field differential in the electrically conductive object, and said first and second eddy field divergence sensor coils overlap.

19. A method of detecting anomalies in an electrically conductive object, said method comprising the steps of:
  establishing a time varying eddy current field in the electrically conductive object using an electromagnetic field emitting member that includes a magnetic flux focusing core, said magnetic flux focusing core having first and second soles that are, in use, placed next adjacent to the electrically conductive object, said first and second poles being spaced apart by a gap;
  monitoring at least first and second regions of the eddy current field at the gap, the first and second regions of the eddy current field at the gap being non-coterminous and non-concentric, the step of monitoring including using a first eddy field divergence sensor coil associated with the first region of the eddy current field at the gap directly to sense eddy field differential in the electrically conductive object at the gap; and
  comparing at least one of
    (a) eddy currents monitored in said first region with eddy currents monitored in said second region; and
    (b) eddy currents monitored in both said first region and said second region with a reference standard for said first region and said second region respectively.

20. The method of claim 19 wherein said method includes one of
  (a) monitoring total eddy current flux through a zone to be examined, and comparing that total eddy current flux to a sum of eddy current fluxes observed in discrete portions of said zone; and
  (b) employing a magnetic flux emitting apparatus to establish said time varying eddy current field; monitoring total eddy current flux through a zone adjacent to the object to be examined, and comparing that total eddy current flux with a measured total emitted flux from the magnetic flux emitting apparatus.

21. The method of claim 19 wherein the first eddy field divergence sensor coil has first and second legs extending radially relative to said core, and third and fourth legs extending on a circumferential arc relative to said core, said third leg extending circumferentially relative to said core at a closer radial distance to said core than said fourth leg, and said step of monitoring includes sensing eddy field differential between said third and fourth legs.

22. The method of claim 19 wherein there is a second eddy field divergence sensor coil associated with the second region, the first region overlaps the second region, and said step of monitoring includes sensing eddy field differential in both said first and second eddy field divergence sensor coils.

23. A process of detection of anomalies in an electrically conductive object, said process comprising:
  providing an anomaly detection apparatus having an electromagnetic field emitting member, said electromagnetic field emitting member including a flux focusing core that includes a first portion and a second portion;
  said first and second portions of said flux focusing core each having a respective proximal end and a distal end;
  said proximal end of said first portion and said proximal end of said second portion being linked together on a continuous magnetic core path,
  said distal end of said first portion and said distal end of said second portion being separated from each other by a gap and defining respective poles of said flux focusing core;
  a power source connected for powering said electromagnetic field emitting member,
  said power source being operable to cause said electromagnetic field emitting member to emit a time varying electromagnetic field;
  said power source having at least a first frequency and a second frequency;
  an array of electromagnetic field sensing members, the members of said array being mounted adjacent to said electromagnetic field emitting member, the field sensing members including a first eddy field divergence sensor coil operable directly to sense eddy field differential in the gap, adjacent to the electrically conductive object;
  monitoring circuitry connected to the members of said array,
  said monitoring circuitry being operable to sense variation of signals as between members of said array; and
  a processor operable to compare signals sensed at said members of said array in response to electromagnetic signals emitted at said first frequency and at said second frequency;
  passing said anomaly detection apparatus adjacent to the electrically conductive object with said distal ends of said first and second portions of said flux focusing core being positioned nearer to the electrically conductive object than said proximal ends of said first and second portions; and
  emitting electromagnetic field signals at more than one frequency from said electromagnetic field emitting member to cause eddy currents to be generated in the electrically conductive object;
  monitoring eddy currents sensed directly by the array of electromagnetic field sensing members at a plurality of positions at the gap; and
  comparing data monitored at the plurality of positions at the gap and at the first and second frequencies to provide an indication of the location of an anomaly in the electrically conductive object.

24. The process of claim 23 wherein the first eddy field divergence sensor coil has first and second legs extending radially relative to said core, and third and fourth legs extending on a circumferential arc relative to said core, said third leg extending circumferentially relative to said core at a closer radial distance to said core than said fourth leg and said process includes using said first eddy field divergence sensor coil to sense eddy field differential directly.

25. The process of claim 23 wherein the array of electromagnetic field sensing members also includes a second eddy field divergence sensor coil operable directly to sense eddy field differential, said first eddy field divergence sensor coil overlaps said second eddy field divergence sensor coil, and said process includes sensing eddy field differential with said first and second eddy field divergence sensor coils.

26. An anomaly detection apparatus for placement next to an electrically conductive object, said anomaly detection apparatus comprising:
an electromagnetic field emitting member, said electromagnetic field emitting member including a magnetic flux focusing core;
a power source connected to said electromagnetic field emitting member, said power source being operable to drive said electromagnetic field emitting member to emit a time varying electromagnetic field;
said power source having at least first and second driving frequencies;
an array of electromagnetic field sensing members, the members of said array being mounted adjacent to said electromagnetic field emitting member;
said array including at least first and second field sensing members, said first and second field sensing members being oriented toward non-coincident regions adjacent to said field emitting member, at least said first electromagnetic field sensing member being non-concentric with said electromagnetic field emitting member, said first electromagnetic field sensing member including an eddy field divergence sensor coil operable to sense directly eddy field differential in the electrically conductive object;
monitoring circuitry connected to the members of said array, said monitoring circuitry being operable to observe differential variation of signals as between members of said array; and
a processor operable to compare signals sensed at said members of said array in response to electromagnetic signals emitted at said first frequency and at said second frequency.

27. The anomaly detection apparatus of claim 26 wherein:
said magnetic flux focusing core includes a first portion and a second portion;
said first portion has a proximal end and a distal end;
said second portion has a proximal end and a distal end;
said proximal end of said first portion and said proximal end of said second portion being linked together on a continuous magnetic core path;
said distal end of said first portion and said distal end of said second portion being separated from each other by a gap;
in operation, said distal ends of said first and second portions being positioned nearer to the electrically conductive object than said proximal ends of said first and second portions; and
said first field sensing member being positioned to measure eddy field divergence at said gap.

28. The anomaly detection apparatus of claim 27 wherein:
said eddy field divergence sensor coil of said first electromagnetic field sensing member includes a first portion that underlies said distal end of said first portion of said magnetic flux focusing core, such that, in use, said first portion of said first eddy field divergence sensor coil is located between said distal end of said first portion of said magnetic flux focusing core and the electrically conductive object; and
said eddy field divergence sensor coil of said first electromagnetic field sensing member includes a second portion that underlies said distal end of said second portion of said magnetic flux focusing core, such that, in use, said second portion of said first eddy field divergence sensor coil is located between said distal end of said second portion of said magnetic flux focusing core and the electrically conductive object.

29. The anomaly detection apparatus of claim 27 wherein:
said distal end of said first portion of said magnetic flux focusing core defines a first pole of said magnetic flux focusing core;
said distal end of said second portion of said magnetic flux focusing core defines a second pole of said magnetic flux focusing core; and
said eddy field divergence sensor coil of said first electromagnetic field sensing member is mounted substantially flush with said first and second poles of said magnetic flux focusing core.

30. The anomaly detection apparatus of claim 27 wherein:
said distal end of said first portion of said magnetic flux focusing core defines a first pole of said magnetic flux focusing core;
said distal end of said second portion of said magnetic flux focusing core defines a second pole of said magnetic flux focusing core; and
said eddy field divergence sensor coil of said first electromagnetic field sensing member is mounted substantially co-planar with said first and second poles of said magnetic flux focusing core.

31. The anomaly detection apparatus of claim 27 wherein:
said first portion of said magnetic flux focusing core is a pole piece;
said second portion of said magnetic flux focusing core is a surrounding wall extending peripherally about said pole piece;
said gap is a peripheral gap between said pole piece and said surrounding wall; and
said eddy field divergence sensor coil of said first electromagnetic field sensing member is positioned to define a closed loop covering a sector of said peripheral gap.

32. The anomaly detection apparatus of claim 27 wherein:
said first portion of said magnetic flux focusing core is a pole piece;
said second portion of said magnetic flux focusing core is a peripheral wall surrounding said pole piece;
said peripheral wall being circular and concentric to said pole piece;
said gap having the shape of an annulus centered on said pole piece; and
said eddy field divergence sensor coil of said first electromagnetic field sensing member is positioned to define a closed loop monitoring a sector of said annular gap.

33. The anomaly detection apparatus of claim 32 wherein:
the magnetic flux focusing core has an axial direction, a radial direction, and a circumferential direction; and
said eddy field divergence sensor coil of said first electromagnetic field sensing member has the form of a four-sided loop that includes a first leg extending in the circumferential direction adjacent to said pole piece, a second leg extending in the circumferential direction adjacent to said peripheral wall, a third leg extending in the radial direction from the first leg to the second leg, and a fourth leg extending in the radial direction from the second leg to the first leg.

34. The anomaly detection apparatus of claim 27 wherein said array of electromagnetic field sensing members includes an electromagnetic field sensing member having an eddy field divergence sensor coil that overlaps the eddy field divergence sensor coil of said first electromagnetic field sensing member.

35. The anomaly detection apparatus of claim 27 wherein said anomaly detection apparatus includes a drive reference coil operable to measure a magnetic field induced in said magnetic flux focusing core by said power source.

36. The anomaly detection apparatus of claim 27 wherein: said anomaly detection apparatus includes a winding extending about said first portion of said magnetic flux focusing core; said winding being positioned in said gap substantially axially flush with said distal ends of said first and second portions of said magnetic flux focusing core; and said winding being operable to sense radial flux thereat.

37. The anomaly detection apparatus of claim 27 wherein:

said distal end of said second portion surrounds said distal end of said first portion;

said gap extends peripherally about said distal end of said first portion; and each of said electromagnetic field sensing members includes a sensing coil defining a closed loop, and each said closed loop covers at least a sector of said gap, all sectors of said gap being associated with at least one said closed loop.

38. The anomaly detection apparatus of claim 27 wherein:

said first portion of said magnetic flux focusing core is a pole piece; said second portion of said magnetic flux focusing core is a surrounding wall extending peripherally about said pole piece;

said gap is a peripheral gap between said pole piece and said surrounding wall; and said eddy field divergence sensor coil of said first electromagnetic field sensing member is a closed loop positioned to monitor a sector of said peripheral gap.

39. The anomaly detection apparatus of claim 27 wherein:

the magnetic flux focusing core has a radial direction and a circumferential direction; and said first portion of said magnetic flux focusing core is a pole piece, said distal end thereof defining a first pole of said magnetic flux focusing core;

said second portion of said magnetic flux focusing core is a peripheral wall surrounding said pole piece, said distal end thereof defining a second pole of said magnetic flux focusing core;

said peripheral wall being a circular wall concentric to said pole piece;

said gap having the shape of an annulus centered on said pole piece;

said eddy field divergence sensor coil of said first electromagnetic field sensing member is a closed loop positioned to monitor a first sector of said peripheral gap;

said eddy field divergence sensor coil of said first electromagnetic field sensing member has the form of a four-sided loop;

said four-sided loop includes a first leg that underlies said distal end of said first portion of said magnetic flux focusing core, such that, in use, said first leg of said eddy field divergence sensor coil is located between said first pole of said magnetic flux focusing core and the electrically conductive object; and said four-sided loop includes a second leg that underlies said distal end of said second portion of said magnetic flux focusing core, such that, in use, said second portion of said eddy current field divergence sensor coil is located between said second pole of said magnetic flux focusing core and the electrically conductive object;

said four-sided loop includes a third leg extending in the radial direction from the first leg to the second leg;

said four-sided loop includes a fourth leg extending in the radial direction from the second leg to the first leg; and said four-sided loop is mounted substantially flush and co-planar with said first and second poles of said magnetic flux focusing core.

40. The anomaly detection apparatus of claim 27 wherein:

the magnetic flux focusing core has a radial direction and a circumferential direction; and said first portion of said magnetic flux focusing core is a pole piece, said distal end thereof defining a first pole of said magnetic flux focusing core;

said second portion of said magnetic flux focusing core is a peripheral wall surrounding said pole piece, said distal end thereof defining a second pole of said magnetic flux focusing core;

said peripheral wall being a circular wall concentric to said pole piece;

said gap having the shape of an annulus centered on said pole piece;

said eddy field divergence sensor coil of said first electromagnetic field sensing member is positioned to define an enclosed loop covering a sector of said annular gap;

said eddy field divergence sensor coil of said first electromagnetic field sensing member has the form of a four-sided loop;

said four-sided loop includes a first leg, said first leg extending in the circumferential direction adjacent to said first portion of said magnetic flux focusing core;

said four-sided loop includes a second leg, said second leg extending in the circumferential direction adjacent to said second portion of said magnetic flux focusing core;

said four-sided loop includes a third leg extending in the radial direction from the first leg to the second leg;

said four-sided loop includes a fourth leg extending in the radial direction from the second leg to the first leg; and said four-sided loop is mounted substantially flush and co-planar with said first and second poles of said magnetic flux focusing core.

41. The anomaly detection apparatus of claim 27 wherein:

said anomaly detection apparatus includes a drive reference coil operable to measure magnetic field induced in said flux focusing core by said power source;

said anomaly detection apparatus includes a winding extending completely around said first portion of said magnetic focusing core;

said winding being positioned in said gap substantially axially flush with said distal ends of said first and second portions of said magnetic flux focusing core; and said winding being operable to sense total radial flux thereat.

42. The anomaly detection apparatus of claim 27 wherein:

said distal end of said second portion surrounds said distal end of said first portion;

said gap extends peripherally about said distal end of said first portion; and each of said electromagnetic field sensing members includes a sensing coil defining a closed loop, and each said closed loop is positioned to monitor a different sector of said gap, all sectors of said gap being monitored by at least one said closed loop.

43. The anomaly detection apparatus of claim 26 wherein:

said magnetic flux focusing core includes a first portion and a second portion;

said first portion has a proximal end and a distal end;

said second portion has a proximal end and a distal end;

said proximal end of said first portion and said proximal end of said second portion being linked together on a continuous magnetic core path;

said distal end of said first portion and said distal end of said second portion being separated from each other by a gap;

said distal end of said first portion of said magnetic flux focusing core defines a first pole of said magnetic flux focusing core;

said distal end of said second portion of said magnetic flux focusing core defines a second pole of said magnetic flux focusing core;

in operation, said distal ends of said first and second portions being positioned nearer to the electrically conductive object than said proximal ends of said first and second portions; and said eddy field divergence sensor coil of said first field sensing member is mounted substantially flush and co-planar with said first and second poles of said magnetic flux focusing core.

44. The anomaly detection apparatus of claim 26 wherein said eddy field divergence sensor coil has first and second legs extending radially relative to said core, and third and fourth legs extending on a circumferential arc relative to said magnetic flux focusing core, said third leg extending circumferentially relative to said magnetic flux focusing core at a closer radial distance to said magnetic flux focusing core than said fourth leg.

45. The anomaly detection apparatus of claim 26 wherein said first electromagnetic field sensing member overlaps said second electromagnetic field sensing member.

* * * * *

UNITED STATES PATENT AND TRADEMARK OFFICE
CERTIFICATE OF CORRECTION

| | | |
|---|---|---|
| PATENT NO. | : 8,274,279 B2 | Page 1 of 1 |
| APPLICATION NO. | : 12/445802 | |
| DATED | : September 25, 2012 | |
| INVENTOR(S) | : Paul D. Gies | |

It is certified that error appears in the above-identified patent and that said Letters Patent is hereby corrected as shown below:

In the Claims:

Claim 4, Column 24, line 15, "soles" should read -- poles --.

Claim 5, Column 24, lines 42-48 should read:
-- (c) said mobile anomaly detector includes a plurality of said electromagnetic field emitters, and said plurality of electromagnetic field emitters includes at least a first emitter and a second emitter, said first and second emitters being movable relative to one another to permit said mobile anomaly detector to girdle the electrically conductive object --.

Claim 10, Column 26, line 5, please delete the word "and".

Claim 10, Column 26, line 11 should read:
-- (i) a substantially planar base; --.

Claim 13, Column 26, line 44, please delete the word "apparatus".

Claim 15, Column 26, line 58, please delete the word "apparatus".

Claim 15, Column 26, lines 60 and 64, "fieldemitter" should read -- field emitter --.

Claim 19, Column 27, line 26, "soles" should read -- poles --.

Claim 26, Column 29, lines 21-22, please delete the words "electro-magnetic".

Signed and Sealed this
Twenty-ninth Day of April, 2014

Michelle K. Lee
*Deputy Director of the United States Patent and Trademark Office*